US009839613B2

(12) United States Patent
Qiao et al.

(10) Patent No.: US 9,839,613 B2
(45) Date of Patent: Dec. 12, 2017

(54) DRY FORMULATIONS OF VACCINES THAT ARE ROOM TEMPERATURE STABLE

(71) Applicant: Intervet Inc., Madison, NJ (US)

(72) Inventors: Zhisong Qiao, Omaha, NE (US); Kevin O'Connell, Omaha, NE (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/024,226

(22) PCT Filed: Sep. 26, 2014

(86) PCT No.: PCT/EP2014/070608

§ 371 (c)(1),
(2) Date: Mar. 24, 2016

(87) PCT Pub. No.: WO2015/044337

PCT Pub. Date: Apr. 2, 2015

(65) Prior Publication Data

US 2016/0228369 A1 Aug. 11, 2016

Related U.S. Application Data

(60) Provisional application No. 61/883,611, filed on Sep. 27, 2013.

(51) Int. Cl.

| | |
|---|---|
| ***A61K 9/16*** | (2006.01) |
| ***C12N 7/00*** | (2006.01) |
| ***A61K 39/155*** | (2006.01) |
| ***A61K 39/23*** | (2006.01) |
| ***A61K 39/175*** | (2006.01) |
| ***A61K 39/235*** | (2006.01) |
| ***A61K 39/295*** | (2006.01) |
| ***A61K 39/12*** | (2006.01) |
| *A61K 39/00* | (2006.01) |

(52) U.S. Cl.

CPC .......... *A61K 9/1623* (2013.01); *A61K 9/1611* (2013.01); *A61K 9/1617* (2013.01); *A61K 9/1658* (2013.01); *A61K 39/12* (2013.01); *A61K 39/155* (2013.01); *A61K 39/175* (2013.01); *A61K 39/23* (2013.01); *A61K 39/235* (2013.01); *A61K 39/295* (2013.01); *C12N 7/00* (2013.01); *A61K 2039/5252* (2013.01); *A61K 2039/5254* (2013.01); *A61K 2039/552* (2013.01); *C12N 2710/10034* (2013.01); *C12N 2710/10334* (2013.01); *C12N 2710/10371* (2013.01); *C12N 2750/14034* (2013.01); *C12N 2750/14071* (2013.01); *C12N 2750/14322* (2013.01); *C12N 2750/14334* (2013.01); *C12N 2760/18034* (2013.01); *C12N 2760/18071* (2013.01); *C12N 2760/18434* (2013.01); *C12N 2760/18471* (2013.01)

(58) Field of Classification Search

None

See application file for complete search history.

(56) References Cited

U.S. PATENT DOCUMENTS

| | | | |
|---|---|---|---|
| 3,133,001 | A | 5/1964 | Muset |
| 3,155,589 | A | 11/1964 | Slater et al. |
| 3,526,696 | A | 9/1970 | Gale |
| 4,337,242 | A | 6/1982 | Markus et al. |
| 4,451,569 | A | 5/1984 | Kobayashi et al. |
| 5,443,959 | A | 8/1995 | Kikuchi et al. |
| 5,565,318 | A | 10/1996 | Walker et al. |
| 5,593,824 | A | 1/1997 | Tremi et al. |
| 5,763,409 | A | 6/1998 | Bayol et al. |
| 5,932,223 | A | 8/1999 | Burke et al. |
| 6,039,958 | A | 3/2000 | Koyama et al. |
| 6,231,860 | B1 | 5/2001 | Fanget et al. |
| 6,331,303 | B1 | 12/2001 | Briggs et al. |
| 6,931,888 | B2 | 8/2005 | Shekunov et al. |
| 7,073,349 | B2 | 7/2006 | Shekunov et al. |
| 7,351,416 | B2 | 4/2008 | Briggs et al. |
| 7,959,929 | B2 | 6/2011 | Crawford et al. |
| 8,008,001 | B2 | 8/2011 | Roerink et al. |
| 8,192,747 | B2 | 6/2012 | Vande Velde |
| 8,227,593 | B2 | 7/2012 | Dobie et al. |
| 8,258,274 | B2 | 9/2012 | Kapil et al. |
| 8,980,610 | B2 | 3/2015 | Selvitelli et al. |
| 9,314,519 | B2 | 4/2016 | Qiao et al. |
| 9,393,298 | B2 | 7/2016 | Buchanan et al. |
| 2004/0038878 | A1 | 2/2004 | Tanikawa et al. |
| 2004/0042971 | A1 | 3/2004 | Truong-Le et al. |
| 2004/0042972 | A1 | 3/2004 | Truong-Le et al. |
| 2004/0154317 | A1 | 8/2004 | Shekunov et al. |

(Continued)

FOREIGN PATENT DOCUMENTS

| | | | |
|---|---|---|---|
| AU | 2013224732 | A1 | 9/2013 |
| EP | 0028563 | A1 | 5/1981 |

(Continued)

OTHER PUBLICATIONS

Burke et al. (Critical Reviews in Therapeutic Drug Carrier Systems. 1999; 16 (1): 1-83).*
Medi (European Pharmaceutical Review. 2014; 19 (1): 16-20).*
Auser et al. (Human Vaccines. 2007; 3 (3): 68-77).*
Morefield (The AAPS Journal. Jun. 2011; 13 (2): 191-200).*
Anonymous, "Nobivac DHPPI"—XP002714517,Retrieved from the Internet: URL:http://www.msd-animal-health.co.nz/binaries/Nobivac DHPPi website label Feb 12 t cm51-37104.pdf - - - —[retrieved on Oct. 10, 2013] the whole document.
Arakawa, et al., Biotechnology applications of amino acids in protein purification and formulations, Amino Acids, 2007, 587-605, 33.

(Continued)

*Primary Examiner* — Shanon A Foley

(57) ABSTRACT

The present invention discloses dry formulations of room temperature stable vaccines that comprise a live attenuated virus, a sugar stabilizer, and an amino acid stabilizer. The present invention also discloses the manufacture of such vaccines and methods of protecting an animal by administration of such vaccines.

20 Claims, No Drawings

(56) References Cited

U.S. PATENT DOCUMENTS

| | | | | |
|---|---|---|---|---|
| 2005/0163803 | A1 | 7/2005 | Warthen et al. | |
| 2005/0178020 | A1 | 8/2005 | Shekunov et al. | |
| 2007/0148765 | A1 | 6/2007 | Evans et al. | |
| 2007/0161085 | A1 | 7/2007 | Trager et al. | |
| 2007/0190163 | A1 | 8/2007 | Malaknov et al. | |
| 2007/0259348 | A1 | 11/2007 | Phadke et al. | |
| 2008/0229609 | A1* | 9/2008 | Bronshtein | A01N 1/0284 34/287 |
| 2008/0248551 | A1 | 10/2008 | Stinchocomb et al. | |
| 2009/0010955 | A1 | 1/2009 | Kapil et al. | |
| 2009/0274734 | A1 | 11/2009 | Daamen et al. | |
| 2010/0015180 | A1 | 1/2010 | Francon et al. | |
| 2010/0068227 | A1* | 3/2010 | Ella | A61K 39/15 424/215.1 |
| 2010/0124557 | A1 | 5/2010 | Oberreither et al. | |
| 2010/0196420 | A1 | 8/2010 | Kapil | |
| 2010/0297231 | A1 | 11/2010 | Vehring et al. | |
| 2011/0016740 | A1 | 1/2011 | Middelbeek et al. | |
| 2011/0064723 | A1 | 3/2011 | Truong-Le et al. | |
| 2011/0081380 | A1 | 4/2011 | Francon et al. | |
| 2011/0113643 | A1 | 5/2011 | Itou et al. | |
| 2012/0049412 | A1 | 3/2012 | Middlebeek et al. | |
| 2012/0213810 | A1 | 8/2012 | Burgard et al. | |
| 2012/0328652 | A1 | 12/2012 | Spibey | |
| 2013/0101619 | A1 | 4/2013 | Cook et al. | |
| 2014/0017318 | A1 | 1/2014 | O'Connell et al. | |
| 2014/0056942 | A1 | 2/2014 | Qiao et al. | |
| 2015/0140102 | A1 | 5/2015 | O'Connell et al. | |
| 2015/0306209 | A1 | 10/2015 | Wasmoen et al. | |
| 2016/0228369 | A1* | 8/2016 | Qiao | A61K 39/295 |

FOREIGN PATENT DOCUMENTS

| | | | |
|---|---|---|---|
| EP | 0650734 | | 10/1993 |
| EP | 1123710 | A1 | 8/2001 |
| EP | 1954308 | B1 | 9/2011 |
| GB | 1575155 | | 9/1980 |
| JP | 61053227 | | 3/1986 |
| WO | 8906973 | A1 | 8/1989 |
| WO | 9704801 | | 2/1997 |
| WO | 03087327 | A2 | 10/2003 |
| WO | 2004017990 | A1 | 3/2004 |
| WO | 2006071563 | A2 | 7/2006 |
| WO | 2007035455 | A2 | 3/2007 |
| WO | 2007056847 | A1 | 5/2007 |
| WO | 2008107908 | A1 | 9/2008 |
| WO | 2008143782 | A1 | 11/2008 |
| WO | 2009109550 | | 9/2009 |
| WO | 2010125084 | A1 | 11/2010 |
| WO | 2010125087 | A1 | 11/2010 |
| WO | 2009092703 | A1 | 6/2011 |
| WO | 2011072218 | | 6/2011 |
| WO | 2011107534 | | 9/2011 |
| WO | 2012007589 | A1 | 1/2012 |
| WO | 2013057235 | A1 | 4/2013 |
| WO | 2014009328 | A1 | 1/2014 |
| WO | 2014029702 | A1 | 2/2014 |
| WO | 2014140239 | A1 | 9/2014 |
| WO | 2015044337 | A2 | 4/2015 |
| WO | 2015121463 | A2 | 8/2015 |
| WO | 2015124594 | A1 | 8/2015 |

OTHER PUBLICATIONS

Brandau, et al., Thermal Stability of Vaccines, Journal of Pharmaceutical Sciences, 2003, 218-231, 92-2.

Cavanagh, et al., Coronavirus avian infectious bronchitis virus, Veterinary Research, 2007, pp. 281-297.

Charles Hong, Occurrence of canine parvovirus type 2c in the United States, J.Vet. Diagn Invest, 2007, 535-539, 19.

Chen, et al., Opportunities and challenges of developing thermostable vaccines, Expert Reviews, 2009, 547-557, 8-5.

Chokephaibulkit et al., Challenges for the formulation of a universal vaccine against dengue, Experimental Biology and Medicine, 2013, pp. 566-578, 238.

Crawford, et al., Transmission of Equine Influenca Virus to Dogs, Science, 2005, 482-485, 310, US.

Derwent; English Abstract of JP61053227; Title: Mixed live vaccine for Japanese encephalitis and swine parvovirus infection; Sasaki; Mar. 17, 1986.

Ellingson, et al., Vaccine efficacy of porcine reproductive and respiratory Syndrome Virus Chimeras, Vaccine, 2010, pp. 2679-2686, 28.

International Search Report for PCT/EP2014/070608, dated May 11, 2015, 6 pages.

Kamerzell, et al., Protein-excipient interactions: Mechanisms and biophysical characterization applied to protein formulation development, Advanced Drug Delivery Reviews, 2011, 1118-1159, 63.

Lee, et al., Dog-bites and local infection with Pasteurella septica, British Medical Journal, 1960, pp. 169-171, 1.5167.

Mochizuki, Masami, Growth characteristics of canine pathogenic viruses in MDCK cells cultured in RPMI 1640 medium without animal protein, Vaccine, 2006, pp. 1744-1748, 24.

Parrish, et al., The origins of new pandemic viruses: The acquisition of new host ranges by canine parvovirus and influenza A viruses, Annual review of microbiology, 2005, pp. 553-586, 59, WO.

Patel, et al., Stability Consideration for Biopharmaceuticals, Part 1, BioProcess Technical, 2011, 1-10.

Pikal, MJ et al., Solid State Chemistry of Proteins: II. The Correlation of Storage Stability of Freeze-Dried Human Growth Hormone (hGH) with Structure and Dynamics in the Glassy Solid, Journal of Pharmaceutical Sciences, 2008, pp. 5106-5121, 97(12).

Schering-Plough Animal Health Ltd., Nobivac DHPPi; Combined Live Attenuated Freeze-Dried Canine Distemper Virus, Adenovirus Type 2, Parvovirus and Parainfluenza Virus Vaccine, Restricted Veterinary Medicine, 2013, XP002714517; 1-2, 1.

Schlehuber, et al., Towards Ambient Temperature-stable vaccines: The identification of thermally stabilizing liquid formulations for measles virus using an innovative high-throughput infectivity assay, Vaccine, 2011, pp. 5031-5039, 29.

Taguchi, et al., Antibody titers for canine parvovirus type-2, canine distemper virus, and canine adenovirus type-1 in adult household dogs, Canine Veterinary Journal, 2011, 983-986, 52.

Tom H. Jin, Improved formulation and lyophilization cycle for rBCG Vaccine, VACCINE, 2011, 4848, 29.

Tompkins, et al., Recombinant parainfluenza virus 5 (PIV5) expressing the influenza A virus, Virology, 2007, pp. 139-150, 16(1).

Zhao Li, Single-Dose Vaccination of a Recombitant Parainfluenza Virus 5 Expressing NP from H5N1 Virus Provides Broad Immunity against Influenza A Viruses, Journal of Virology, 2013, 5985-5993, 87-10.

* cited by examiner

DRY FORMULATIONS OF VACCINES THAT ARE ROOM TEMPERATURE STABLE

CROSS-REFERENCE TO RELATED APPLICATIONS

This application is a national stage entry under 35 U.S.C. §371 of PCT/EP2014/070608 filed on Sep. 26, 2014, which claims priority under 35 U.S.C. §119(e) of provisional application U.S. Ser. No. 61/883,611 filed Sep. 27, 2013, the contents of both of which are hereby incorporated by reference in their entireties.

FIELD OF THE INVENTION

The present invention pertains to room temperature stable dry formulations of vaccines that comprise one or more live attenuated viruses. The invention also pertains to the manufacture of such dry formulations of vaccines and methods of vaccinating animal subjects with the vaccines.

BACKGROUND

Live attenuated viruses are unstable when stored at room temperature for extended time periods. Therefore, most live attenuated virus vaccines are freeze-dried and refrigerated prior to use. However, shipping and storage of such vaccines leads to significant extra costs that must be passed on to vaccine dispensaries, veterinarians, livestock handlers/farmers, and ultimately to the pet owner or the consumer. Such costs can prove prohibitive in poor communities and third world countries. Accordingly, WHO requires a minimal survival of >20% after 28 days at 37° C. for the human BCG vaccine [see e.g., Jin et al., *Vaccine* 29:4848-4852 (2011)].

There are a significant number of viruses that can infect either companion animals (such as dogs, cats, and horses) or livestock (such as poultry, cattle, and swine). For example, whereas symptoms due to the corresponding virus infections can include mild cold-like symptoms, others can be rapidly fatal, as in the case of canine distemper virus (CDV) infections [see e.g., US2010/0196420]. Indeed, CDV triggers a multi-systemic infection that may involve the ocular, respiratory, gastrointestinal, integument, and nervous systems. The mortality rate from canine parvovirus (CPV) is also relatively high [see e.g., US2009/0010955]. CPV is primarily an enteric pathogen that infects dogs, especially young dogs, and is characterized by acute diarrhea, fever, and leukopenia in dogs and puppies more than 4 to 5 weeks old. Even younger puppies can suffer myocardial disease. Canine distemper virus and canine parvovirus are the two most important canine viruses to protect puppies/dogs from.

Additional canine viruses include: canine parainfluenza (CPI) virus, which is a highly contagious virus that causes respiratory illnesses contributing to the contraction of upper respiratory diseases and infectious tracheobronchitis; canine adenovirus type-1 (CAV1) which leads to infectious hepatitis; and canine influenza virus (CIV) which is highly contagious and can cause a severe type of respiratory disease. CIV has been reported to be capable of causing 100% infection with 80% morbidity, and up to 5-8% mortality in severe infections [Crawford et al., *Science* 310 (5747):482-485 (2005); U.S. Pat. No. 7,959,929 B2]. Similarly, there are a number of feline viruses that afflict cats including feline calicivirus (FCV), feline leukemia virus (FeLV), feline panleukopenia virus (FPLV), feline coronavirus (FCoV), and feline rhinotracheitis (FVR) virus.

There also are a significant number of viruses that can infect cattle. Such viruses include bovine viral diarrhea virus types 1 and 2, (BVDV1 and BVDV2), infectious bovine rinotracheitis (IBR) virus, parainfluenza type 3 (PI3), bovine respiratory syncytial virus (BRSV), and bovine respiratory coronavirus (BRCV). In addition, there are a number of bacteria that can infect cattle too, including *Pasteurella multocida, Mannheimia haemolytica, Histophilus somni*, and *Mycoplasma bovis.*

Similarly, there are a significant number of viruses that can infect poultry. Such viruses include infectious bronchitis virus (IBV), infectious bursal disease virus (IBDV), Newcastle disease virus (NDV), Infectious Laryngotracheitis (ILTV), Mareks disease virus (MDV), Herpes Virus of Turkeys (HVT) which is also known as MDV3, and avian metapneumoviruses (aMPV). In addition, there are a number of bacteria that can infect poultry too, including *Pasteurella multocida, Salmonella* ssp., *Escherichia coli, Mycoplasma* ssp., *Avibacterium paragallinararum, Erysipelas* ssp., *Campylobacter* ssp., *Vibrio* ssp., *Clostridium perfringens* and parasites such as *Eimeria.*

Moreover, there are a number of viruses that can infect swine. Such viruses include porcine reproductive and respiratory syndrome virus (PRRS), porcine circovirus (PCV), transmissible gastroenteritis virus (TGE), porcine pseudorabies virus (PPRV), porcine parvovirus (PPV), swine influenza virus (SIV), porcine rotavirus (PRV) and porcine epidemic diarrhea virus (PED). In addition, there are a number of bacteria that can infect swine too, including *Pasteurella multocida* of multiple serotypes, *Salmonella* ssp., *Escherichia coli* of multiple pillus types, *Haemophilus parasuis, Lawsonia intracellularis, Mycoplasma* ssp., *Bordetella bronchiseptica, Erysipelas* ssp., *Campylobacter* ssp., *Actinobacillus pleuropneumonia., Clostridium perfringens* and *Clostridium difficile.*

It is now widely accepted that the best way of preventing disease due to virus infections in an animal is to vaccinate that animal against these viruses. Just as one example, in dogs canine distemper virus vaccines have significantly reduced the prevalence of the corresponding disease. Similarly, infectious canine hepatitis has been extremely limited by canine adenovirus-2 vaccines (CAV2). The use of live attenuated CAV2 in vaccines in place of closely related CAV1 eliminates concerns regarding the interstitial nephritis and corneal opacity observed in dogs that have been inoculated with live attenuated CAV1 [Taguchi et al., *Can Vet J.* 52(9): 983-986 (2011)]. Moreover, multivalent live attenuated virus vaccines can be safely administered that limit the number of vaccine injections required. Accordingly, there are several commercially available multivalent live attenuated canine virus vaccines that protect against canine distemper, canine infectious hepatitis, canine parvovirus, and canine parainfluenza virus. In addition, newer multivalent vaccines further protect against canine influenza virus as well. However, there remains a great need for attenuated live viral vaccines, such as canine viral vaccines, that can be shipped and stored at room temperature.

The citation of any reference herein should not be construed as an admission that such reference is available as "prior art" to the instant application.

SUMMARY OF THE INVENTION

In order to overcome the deficiencies of current vaccines, the present invention provides novel stable dry formulations of live, attenuated vaccines, e.g., virus vaccines, which can be shipped and/or stored at room temperature, as well as their corresponding immunogenic compositions. These dry formulations remain efficacious at 27° C. for extended periods, such as 12 months, 18 months, or even longer (e.g., 1.5 to 3 years).

In certain embodiments, the live, attenuated vaccine is an avian vaccine. In particular embodiments of this type, the live, attenuated avian vaccine is a poultry vaccine comprising a live, attenuated poultry virus. In more particular embodiments of this type, the live, attenuated poultry vaccine is a chicken vaccine comprising a live, attenuated chicken virus. In an alternative embodiment of this type the live, attenuated poultry vaccine is a turkey vaccine comprising a live, attenuated turkey virus.

In certain embodiments, the live, attenuated vaccine is a mammalian vaccine. In particular embodiments of this type, the live, attenuated mammalian vaccine is a human vaccine comprising a live, attenuated human virus. In other such embodiments, the live, attenuated mammalian vaccine is a bovine vaccine comprising a live, attenuated bovine virus. In yet other embodiments, the live, attenuated mammalian vaccine is a porcine vaccine comprising a live, attenuated porcine virus.

In still other embodiments, the live, attenuated mammalian vaccine is a companion animal vaccine. In particular embodiments of this type, the live, attenuated companion animal vaccine is a canine vaccine. In other embodiments of this type, the live, attenuated companion animal vaccine is a feline vaccine. In still other embodiments, the live, attenuated companion animal vaccine is an equine vaccine. Accordingly, in particular embodiments, the live attenuated canine vaccine comprises a live attenuated canine virus. In other embodiments, the live attenuated feline vaccine comprises a live attenuated feline virus. In yet other embodiments, the live attenuated equine vaccine comprises a live attenuated equine virus.

In other embodiments the live attenuated vaccine comprises a recombinant virus. In particular embodiments of this type the recombinant virus is employed as a recombinant vector that encodes a heterologous protein. In more particular embodiments of this type, the heterologous protein is a viral or bacterial antigen. The present invention further provides methods of making the stable dry formulations of the present invention. The present invention further provides methods of storing the vaccines of the present invention prior to use at 27° C. for extended periods, such as 12 months or longer (e.g., 1.5 to 3 years) as stable dry formulations.

The present invention also provides methods of administering to an animal the stable dry formulations of the present invention. In particular embodiments the stable dry formulation is reconstituted into a liquid vaccine prior to administration. The present invention further provides methods of preventing a disease in an animal (i.e., human, companion animal, or livestock animal) through administering the dry formulation (e.g., in the form of a powder) and/or the reconstituted liquid vaccine of the present invention. In particular embodiments, the companion animal is a canine. In related embodiments, the companion animal is a feline. In yet other embodiments, the companion animal is a horse. In still other embodiments, the livestock animal is a bovine. In yet other embodiments, the livestock animal is a pig. In still other embodiments, the livestock animal is a chicken. In yet other embodiments, the livestock animal is a turkey.

Accordingly, the present invention provides dry formulations of vaccines that are room temperature stable that comprise a live attenuated virus. In particular embodiments, the dry formulations of the vaccine comprise a sugar stabilizer. In related embodiments of this type, the vaccine comprises 15% to 80% (w/w) sugar stabilizer. In particular embodiments, the dry formulations of the vaccine comprises 30% to 80% (w/w) sugar stabilizer. In other particular embodiments, the vaccine comprises 40% to 80% (w/w) sugar stabilizer. In certain embodiments, the vaccine comprises 25% to 50% (w/w) sugar stabilizer. In related embodiments the vaccine comprises 30% to 70% (w/w) sugar stabilizer. In even more particular embodiments, the vaccine comprises 40% to 60% (w/w) sugar stabilizer.

In certain embodiments the sugar stabilizer is a non-reducing oligosaccharide. In particular embodiments of this type, the non-reducing oligosaccharide is sucrose. In yet other embodiments, the non-reducing oligosaccharide is trehalose. In still other embodiments, the non-reducing oligosaccharide is raffinose. In other embodiments the sugar stabilizer is a sugar alcohol. In a particular embodiment of this type the sugar alcohol is sorbitol. In other embodiments, the sugar alcohol is xylitol. In still other embodiments, the sugar alcohol is maltitol.

In alternative embodiments the sugar stabilizer is actually a combination of two or more sugar stabilizers. In particular embodiments of this type, the sugar stabilizer is a combination of sucrose and sorbitol. In certain embodiments, the sugar stabilizer is a combination of sucrose and trehalose. In still other embodiments, the sugar stabilizer is a combination of trehalose and sorbitol. In yet other embodiments, the sugar stabilizer is a combination of sucrose, trehalose, and sorbitol.

The room temperature stable dry formulations of the vaccines of the present invention can further comprise one or more bulking stabilizers. In particular embodiments, the amount of the bulking stabilizers in the vaccines is 1% to 6% (w/v) in the liquid form of the vaccine and 2% to 25% (w/w) in the dry formulation. In certain embodiments, the bulking stabilizer is mannitol. In related embodiments the bulking stabilizer is glycine. In particular embodiments the bulking stabilizer is dextran. In certain embodiments the bulking stabilizer is maltodextrin. In particular embodiments the bulking stabilizer is dextrose. In other embodiments the bulking stabilizer is polyvinylpyrrolidone. In still other embodiments the bulking stabilizer is hydroxyethyl starch. In yet other embodiments the vaccines comprise a combination of bulking stabilizers. In certain embodiments the bulking stabilizer comprises two or more of the following: dextran, mannitol, glycine, maltodextrin, polyvinylpyrrolidone, and hydroxyethyl starch. In particular embodiments of this type, the bulking stabilizer comprises mannitol and glycine. In related embodiments, the bulking stabilizer comprises dextran and glycine. In still other embodiments of this type, the bulking stabilizer comprises mannitol, dextran, and glycine.

In particular embodiments, the protein stabilizer is gelatin. In other embodiments the protein stabilizer is a hydrolysate of whole casein. In particular embodiments the hydrolysate of whole casein is a proteolytic hydrolysate of whole casein. In yet other embodiments the protein stabilizer is a combination of both gelatin and a proteolytic hydrolysate of whole casein.

The room temperature stable dry formulations of the vaccines of the present invention can range in pH from pH 5.5 to pH 8.5. In particular embodiments the pH range is from pH 6.0 to pH 8.0. In certain embodiments the pH range is from pH 6.5 to pH 7.8. In particular embodiments the pH range is from pH 6.8 to pH 7.5. In other embodiments the pH range is from pH 6.0 to pH 7.6. In yet other embodiments the pH range is from pH 6.0 to pH 6.8. In still other particular embodiments the pH range is from pH 7.0 to pH 7.4. In more particular embodiments the pH is pH 7.2. In other more particular embodiments the pH is pH 6.5.

The room temperature stable dry formulations of the vaccines of the present invention can comprise a buffer. In a particular embodiment of this type, the buffer comprises 0.1% to 2% (w/w) histidine (2.5 to 50 mM prior to drying). In a related embodiment, the buffer comprises 0.2% to 1% (w/w) histidine. In particular embodiments, the buffer comprises 0.25% to 0.75% (w/w) histidine. In more particular embodiments the buffer comprises 0.5% (w/w) histidine.

In other embodiments the buffer comprises 0.1% to 2% (w/w) phosphate (either sodium phosphate, potassium phosphate, or a mixture of the two; 2.5 to 50 mM prior to drying). In related embodiments, the buffer comprises 0.2% to 1% (w/w) phosphate. In particular embodiments, the buffer comprises 0.25% to 0.75% (w/w) phosphate. In more specific embodiments the buffer comprises 0.5% (w/w) phosphate.

In yet other embodiments the buffer can comprise 2.5 to 50 mM Tris. In particular embodiments the buffer comprises 2.5 to 50 mM Tris and 2.5 to 50 mM histidine. In more particular embodiments the buffer comprises 5 to 20 mM Tris and 5 to 20 mM histidine. In still more particular embodiments the buffer comprises 7.5 to 15 mM Tris and 7.5 to 15 mM histidine.

The room temperature stable dry formulations of the vaccines of the present invention also can comprise an amino acid stabilizer. In particular embodiments the amino acid stabilizer is arginine. In yet other embodiments, the amino acid stabilizer is glutamic acid. In still other embodiments the amino acid stabilizer is aspartic acid. In yet other embodiments, the amino acid stabilizer is lysine. In related embodiments, the room temperature stable dry formulations of the vaccines of the present invention comprise two or more amino acid stabilizers. In a particular embodiment of this type the amino acid stabilizer is arginine and glutamate.

In certain embodiments the concentration of the amino acid stabilizer in the vaccine is 0.1-0.4M in the liquid formulation [10%-40% (w/w) in the dry formulation]. In particular embodiments the concentration of the amino acid stabilizer in the vaccine is 0.25-0.35M in the liquid formulation. In more particular embodiments the concentration of the amino acid stabilizer in the vaccine is 0.25-0.35M in the liquid formulation. In even more particular embodiments the amino acid stabilizer is 0.3M arginine in the liquid formulation.

The room temperature stable dry formulations of the vaccines of the present invention also can comprise a protein stabilizer. The protein stabilizer can be an intact protein and/or a protein hydrolysate. In particular embodiments the stabilizer protein is gelatin. In alternative embodiments the protein stabilizer is a hydrolysate of whole casein. In certain embodiments the hydrolysate of whole casein is a proteolytic hydrolysate of whole casein. In particular embodiments, the dry formulation comprises 2% to 20% (w/w) of the protein stabilizer. In other particular embodiments, the protein stabilizer comprises 1% to 10% (w/w) gelatin. In still other particular embodiments the protein stabilizer comprises 1% to 10% (w/w) of a hydrolysate of whole casein.

The dry formulations of vaccines of the present invention also can comprise a protein stabilizer that includes both gelatin and a hydrolysate of whole casein. In particular embodiments of this type, the protein stabilizer comprises 1% to 10% (w/w) gelatin and 1% to 10% (w/w) of a hydrolysate of whole casein. In more particular embodiments, the protein stabilizer comprises 2% to 5% (w/w) gelatin and 2% to 6% (w/w) of a hydrolysate of whole casein. In other particular embodiments, the protein stabilizer comprises 0.4% to 3.0% gelatin (w/w) and 0.5% to 3.0% (w/w) of a hydrolysate of whole casein. In specific embodiments the protein stabilizer comprises 2.3% (w/w) gelatin and 2.8% (w/w) of a hydrolysate of whole casein. In other specific embodiments, the protein stabilizer comprises 3.3% (w/w/) gelatin and 4.2% (w/w) of a hydrolysate of whole casein.

Any of the dry formulations of present invention can further comprise 0.02% to 1% (w/w) of a salt of a divalent cation. In particular embodiments the divalent cation is 1 mM-5 mM in the liquid form and 0.1%-0.5% (w/w) in the dried formulation. In certain embodiments, the divalent cation is magnesium ($Mg^{++}$). In other embodiments the divalent cation is calcium ($Ca^{++}$). In still other embodiments the divalent cation is zinc ($Zn^{++}$). In yet other embodiments the divalent cation is a mixture of $Mg^{++}$, and/or $Ca^{++}$, and/or $Zn^{++}$.

Any of the room temperature stable dry formulations of the vaccines of the present invention can further comprise one or more osmolytes. In particular embodiments the osmolyte is ectoine. In other particular embodiments the osmolyte is hydroxyectoine. In yet other embodiments the osmolyte is a combination of ectoine and hydroxyectoine. In particular embodiments, the percentage of the osmolyte in the formulation is 0.2% to 7.5% (w/w). In more particular embodiments, the percentage of the osmolyte in the formulation is 0.5% to 5% (w/w). In still more particular embodiments, the percentage of the osmolyte in the formulation is 1% to 3% (w/w).

The room temperature stable dry formulations of the vaccines of the present invention can comprise a live attenuated virus. In one aspect of the present invention the live attenuated virus is a canine virus. In a related embodiment the live attenuated virus is a feline virus. In another embodiment the live attenuated virus is an equine virus.

In yet another aspect of the present invention the live attenuated virus is a liestock animal virus, e.g., food animal virus. In one such embodiment the live attenuated virus is a poultry virus. In particular embodiments of this type the poultry virus is a chicken virus. In other embodiments of this type the poultry virus is a turkey virus. In other such embodiments, the live attenuated virus is a bovine virus. In still other embodiments, the live attenuated virus is a porcine virus.

In certain embodiments the live attenuated virus is distemper virus (CDV). In other embodiments the live attenuated virus is adenovirus. In yet other embodiments the live attenuated virus is a parvovirus. In still other embodiments the live attenuated virus is parainfluenza virus (CPI). In yet other embodiments the live attenuated virus is an influenza virus.

In still another aspect of the present invention the live attenuated virus is a canine virus. In certain embodiments the live attenuated canine virus is canine distemper virus (CDV). In other embodiments the live attenuated canine virus is canine adenovirus type 2 (CAV2). In yet other embodiments the live attenuated canine virus is canine parvovirus (CPV). In one particular embodiment of this type, the canine parvovirus is a canine parvovirus 2 (CPV-2). In another particular embodiment of this type, the canine parvovirus is a canine parvovirus 2a (CPV-2a). In yet another particular embodiment of this type, the canine parvovirus is a canine parvovirus 2b (CPV-2b). In still another particular embodiment of this type, the canine parvovirus is a canine parvovirus 2c (CPV-2c). In a specific embodiment of this type, the CPV-2c is ATCC accession No. PTA-13492. In yet another embodiment the canine parvovirus is a recombinant canine parvovirus that has been constructed to comprise a heterogenous CPV-2c/CPV-2 genome, i.e., the region encoding the capsid proteins is from a CPV-2c isolate and the region encoding the nonstructural proteins is from a CPV-2 isolate [see, U.S. 2012/0328652 A1, the contents of which are hereby incorporated by reference in their entireties, in which the nucleotide sequence encoding the capsid protein in the CPV-2 genome has been replaced by the nucleotide sequence encoding the capsid protein of a CPV-2c, thereby resulting in the heterogenous CPV-2c/CPV-2 genome]. In still other embodiments the live attenuated canine virus is canine parainfluenza virus (CPI).

The present invention also includes recombinant virus vectors. In particular embodiments the recombinant virus vector is a recombinant parainfluenza virus vector. In certain embodiments the recombinant parainfluenza virus vector is a recombinant canine parainfluenza virus vector. In particular embodiments the recombinant parainfluenza virus (e.g., a recombinant canine parainfluenza virus vector) encodes and expresses a heterologous protein. In certain embodiments of this type, the heterologous protein is a non-canine antigen. In more particular embodiments the non-canine antigen is a poultry viral or poultry bacterial antigen. In other embodiments the non-canine antigen is a porcine viral or porcine bacterial antigen. In still other embodiments the non-canine antigen is a bovine viral or bovine bacterial antigen. In yet other embodiments the non-canine antigen is a feline viral or feline bacterial antigen. In certain embodiments, the recombinant parainfluenza virus is a recombinant parainfluenza Virus 5.

In yet other embodiments the live attenuated canine virus is canine coronavirus. In still other embodiments the live attenuated canine virus is canine pneumovirus. In yet other embodiments the live attenuated canine virus is infectious canine hepatitis virus. In still other embodiments the live attenuated canine virus is canine herpes virus. In yet other embodiments the live attenuated canine virus is rabies virus. In still other embodiments the live attenuated canine virus is canine minute virus. In yet other embodiments the live attenuated canine virus is canine influenza virus. In alternative embodiments the live attenuated virus is pseudorabies virus.

The room temperature stable dry formulations of the vaccines of the present invention can comprise a live attenuated feline virus. In certain embodiments the live attenuated feline virus is feline herpesvirus (FHV). In other embodiments the live attenuated feline virus is feline calicivirus (FCV). In yet other embodiments the live attenuated feline virus is feline pneumovirus (FPN). In still other embodiments the live attenuated feline virus is feline parvovirus (FPV). In yet other embodiments the live attenuated feline virus is feline leukemia virus (FeLV). In still other embodiments the live attenuated feline virus is feline infectious peritonitis virus (FIPV). In yet other embodiments the live attenuated feline virus is feline immunodeficiency virus (FIV). In still other embodiments the live attenuated feline virus is borna disease virus (BDV). In yet other embodiments the live attenuated feline virus is feline influenza virus. In still other embodiments the live attenuated feline virus is feline panleukopenia virus (FPLV). In yet other embodiments the live attenuated feline virus is feline coronavirus (FCoV). In still other embodiments the live attenuated feline virus is feline rhinotracheitis virus (FVR).

In addition, the present invention provides room temperature stable dry formulations of vaccines that are multivalent vaccines. In particular embodiments the multivalent vaccines of the present invention comprise only live attenuated virus vaccines. Such multivalent vaccines can contain any combination of live attenuated viruses. In particular embodiments of this type, the multivalent vaccine comprises live attenuated canine distemper virus and live attenuated canine parvovirus. In related embodiments the multivalent vaccine comprises live attenuated canine distemper virus and live attenuated canine adenovirus type 2. In other embodiments the multivalent vaccine comprises live attenuated canine distemper virus and live attenuated canine parainfluenza virus. In still other embodiments the multivalent vaccine comprises live attenuated canine distemper virus, live attenuated canine parvovirus, and live attenuated canine parainfluenza virus. In yet other embodiments the multivalent vaccine comprises live attenuated canine distemper virus, live attenuated canine parvovirus, and live attenuated canine adenovirus type 2. In still other embodiments the multivalent vaccine comprises live attenuated canine distemper virus, live attenuated canine parainfluenza virus, and live attenuated canine adenovirus type 2. In yet other embodiments the multivalent vaccine comprises live attenuated canine distemper virus, live attenuated canine parvovirus, live attenuated canine parainfluenza virus, and live attenuated canine adenovirus type 2. In particular embodiments the multivalent vaccine comprises live attenuated canine distemper virus, live attenuated canine parvovirus, live attenuated canine parainfluenza virus, live attenuated canine adenovirus type 2, and live attenuated canine coronavirus. In related embodiments the multivalent vaccine comprises live attenuated canine distemper virus, live attenuated canine parvovirus, live attenuated canine parainfluenza virus, live attenuated canine adenovirus type 2, and live attenuated feline coronavirus. In particular embodiments of this type, the multivalent vaccine comprises live attenuated canine distemper virus, live attenuated canine adenovirus type 2, live attenuated canine parvovirus, live attenuated canine parainfluenza virus, and live attenuated canine influenza virus.

In other embodiments the present invention provides room temperature stable dry formulations of multivalent vaccines that comprise live attenuated adenovirus type 2 and live attenuated canine parainfluenza virus. In yet other embodiments the multivalent vaccine comprises live attenuated canine adenovirus type 2 and live attenuated canine parvovirus. In yet other embodiments the multivalent vaccine comprises live attenuated canine parvovirus and live attenuated canine parainfluenza virus. In still other embodiments the multivalent vaccine comprises live attenuated canine adenovirus type 2, live attenuated canine parvovirus, and live attenuated canine parainfluenza virus. In particular embodiments of this type, the multivalent vaccine comprises live attenuated canine adenovirus type 2, live attenuated canine parvovirus, live attenuated canine parainfluenza virus, and live attenuated canine influenza virus.

In other embodiments the present invention provides room temperature stable dry formulations of multivalent vaccines that comprise live attenuated canine adenovirus type 2 and live attenuated canine parainfluenza virus. In yet other embodiments the multivalent vaccine comprises live attenuated canine adenovirus type 2 and live attenuated canine parvovirus. In yet other embodiments the multivalent vaccine comprises live attenuated canine parvovirus and live attenuated canine parainfluenza virus. In still other embodiments the multivalent vaccine comprises live attenuated canine adenovirus type 2, live attenuated canine parvovirus, and live attenuated canine parainfluenza virus. In particular embodiments of this type, the multivalent vaccine comprises live attenuated canine adenovirus type 2, live attenuated canine parvovirus, live attenuated canine parainfluenza virus, and live attenuated canine influenza virus.

In any of the aforementioned embodiments the live attenuated canine virus can be a recombinant virus vector. In particular embodiments, the recombinant virus vector is a recombinant canine parainfluenza virus vector. In particular embodiments of this type, the recombinant canine parainfluenza virus vector encodes and expresses a heterologous antigen.

In other specific embodiments the dry formulations of a multivalent vaccine that comprise a canine parvovirus (CPV) can further comprise 0.5% to 5% (w/w) sorbitol.

In particular embodiments the titer of a live attenuated virus in the dry formulations of a vaccine (or of each of the viruses in a multivalent vaccine) of the present invention is $1\times10^3$ to $1\times10^{10}$. In more particular embodiments the titer is $1\times10^4$ to $1\times10^9$. In still more particular embodiments, the titer is $5\times10^4$ to $1\times10^8$.

Accordingly, the present invention provides dry formulations of a vaccine that comprise a live attenuated virus (e.g., canine virus, or feline virus, or equine virus, or porcine virus, or bovine virus, or poultry virus), 30% to 80% (w/w) of a non-reducing oligosaccharide, 6% to 40% (w/w) of an amino acid stabilizer, 2% to 20% (w/w) of a protein stabilizer, and a buffer having a pH of 6.0 to 8.0. In particular embodiments the dry formulations remain efficacious for at least 18 months at 27° C. In related embodiments the dry formulations further comprise 2% to 25% (w/w) of a bulking stabilizer. In particular embodiments of this type, the ratio of the bulking stabilizer to the non-reducing oligosaccharide and/or sugar alcohol is 0.025 to 0.60. In more particular embodiments, the ratio of the bulking stabilizer to the non-reducing oligosaccharide and/or sugar alcohol is 0.05 to 0.40. In still more particular embodiments, the ratio of the bulking stabilizer to the non-reducing oligosaccharide and/or sugar alcohol is 0.075 to 0.30. In even more particular embodiments, the ratio of the bulking stabilizer to the non-reducing oligosaccharide and/or sugar alcohol is 0.1 to 0.25.

In particular embodiments, a non-reducing oligosaccharide of a dry formulation of a vaccine of the present invention comprises sucrose and/or trehalose, and/or raffinose. In certain embodiments of this type the pH of the dry formulation is pH 6.0 to 7.6. In particular embodiments of the present invention, the bulking stabilizer is mannitol. In related embodiments the amino acid stabilizer is arginine. In certain embodiments of this type the amino acid stabilizer further comprises glutamate.

In specific embodiments the dry formulation of a vaccine of the present invention comprises a combination of 20% to 80% (w/w) sucrose and 18% to 66% (w/w) trehalose as the non-reducing oligosaccharide, 5% to 20% (w/w) mannitol as the bulking stabilizer, 9% to 34% (w/w) amino acid stabilizer, a combination of 2% to 5% (w/w) gelatin, and 2% to 6% (w/w) of a proteolytic hydrolysate of whole casein as the protein stabilizer, and a buffer at pH 6.2 to 7.5. In particular embodiments of this type, the ratio of the bulking stabilizer to the non-reducing oligosaccharide is 0.08 to 0.37.

In more specific embodiments, the non-reducing oligosaccharide is a combination of 45% to 60% (w/w) sucrose and 15% to 25% (w/w) trehalose, the bulking stabilizer is 5% to 17% (w/w) mannitol, the amino acid stabilizer is 10% to 25% (w/w) arginine; the protein stabilizer comprises 1.5% to 3.5% (w/w) gelatin and 2% to 4% (w/w) of a proteolytic hydrolysate of whole casein, and a buffer at pH 6.2 to 7.5. In particular embodiments of this type, the ratio of the bulking stabilizer to the non-reducing oligosaccharide is 0.1 to 0.3.

In certain embodiments the dry formulation of a canine vaccine of the present invention comprises live attenuated canine distemper virus (CDV), canine adenovirus type 2 (CAV2), and canine parainfluenza virus (CPI); a combination of 15% to 80% (w/w) sucrose and 15% to 80% (w/w) trehalose as the non-reducing oligosaccharide, with the combined amount of sucrose and trehalose being 30% to 80% (w/w); 2% to 25% (w/w) mannitol as the bulking stabilizer, with the ratio of the total bulking stabilizer to the total non-reducing oligosaccharide being 0.05 to 0.4; the protein stabilizer being a combination of 1% to 10% (w/w) gelatin with 1% to 10% (w/w) of a proteolytic hydrolysate of whole casein; 6% to 40% (w/w) arginine as the amino acid stabilizer; and a buffer at pH 6.2 to 7.5. In specific embodiments of this type, the dry formulation further comprises one or more, or all of the following: (i) 0.5% to 5.0% ecotoine, (ii) 5% to 15% glutamate, (iii) 0.02% to 1% $MgSO_4$, and (iv) live attenuated canine parvovirus (CPV) with 2% to 5% sorbitol. In more specific embodiments the buffer is 0.1% to 2% potassium or sodium phosphate, pH 6.2 to 7.5.

In more particular embodiments the dry formulation of a canine vaccine of the present invention comprises live attenuated CDV, CAV2, and CPI; a combination of 20% to 80% (w/w) sucrose and 18% to 66% (w/w) trehalose as the non-reducing oligosaccharide, with the combined amount of sucrose and trehalose being 45% to 79% (w/w); 5% to 17% (w/w) mannitol as the bulking stabilizer, with the ratio of the total bulking stabilizer to the total non-reducing oligosaccharide being 0.08 to 0.37; the protein stabilizer being a combination of 2% to 5% (w/w) gelatin with 2% to 6% (w/w) of a proteolytic hydrolysate of whole casein; the amino acid stabilizer being 9% to 34% (w/w) arginine; and a buffer at pH 6.5 to 7.2.

In specific embodiments of this type, the dry formulation further comprises one or more, or all of the following: (i) 1% to 3% ecotoine, (ii) 7% to 12% glutamate, (iii) 0.05% to 0.5% $MgSO_4$, and (iv) live attenuated CPV with 3% to 4% sorbitol. In specific embodiments the buffer is 0.2% to 1% potassium or sodium phosphate, pH 6.5 to 7.2. In certain embodiments of these types, the dry formulation of the vaccine remains efficacious for at least 18 months at 27° C.

In an alternative aspect, the present invention provides dry formulations of vaccines that comprise a live attenuated parvovirus, e.g., canine parvovirus (CPV), 10% to 80% (w/w) of a sugar alcohol, 10% to 70% (w/w) of a bulking stabilizer, 4% to 50% (w/w) of a protein stabilizer, and a buffer having a pH of 6.8 to 8.0. In particular embodiments of this type the dry formulation further comprises 10% to 50% (w/w) of an amino acid stabilizer. In certain embodiments, the dry formulation of the vaccine remains efficacious for at least 18 months at 27° C.

In more particular embodiments, the present invention provides dry formulations of vaccines that comprise a live attenuated parvovirus, e.g., CPV, 23% to 49% (w/w) of a sugar alcohol, 16% to 50% (w/w) of a bulking stabilizer, 7% to 36% (w/w) of a protein stabilizer, and a buffer having a pH of 7.0 to 7.4. In even more particular embodiments of this type the dry formulation further comprises 25% to 36% (w/w) of an amino acid stabilizer. In certain embodiments, the dry formulation of the vaccine remains efficacious for at least 18 months at 27° C.

The sugar alcohol of the dry formulations of these monovalent parvovirus vaccines, e.g., monovalent CPV vaccines, can be sorbitol, mannitol, xylitol, maltitol, and combinations thereof, the bulking stabilizer can be dextran, maltodextrin, polyvinylpyrrolidone, hydroxyethyl starch, glycine, or any combination thereof. The protein stabilizer can be gelatin, a hydrolysate of whole casein, or a combination of the two. In certain embodiments of this type, the hydrolysate of whole casein is a proteolytic hydrolysate of whole casein. In particular embodiments the sugar alcohol is sorbitol, the bulking stabilizer is a combination of dextran and glycine, and the protein stabilizer is a combination of gelatin and a proteolytic hydrolysate of whole casein.

In more particular embodiments, the present invention provides dry formulations of vaccines that comprise a live attenuated parvovirus, e.g., CPV, 10% to 80% (w/w) of sorbitol as the sugar alcohol, a combination of 5% to 30% (w/w) of glycine and 5% to 40% (w/w) of dextran as the bulking stabilizer, a combination of 2% to 25% (w/w) gelatin with 2% to 25% (w/w) of a proteolytic hydrolysate of whole casein as the protein stabilizer; and a buffer having a pH of 6.5 to 7.8. In certain embodiments of this type, 10% to 50% (w/w) arginine is included as an amino acid stabilizer. In specific embodiments, the buffer is 0.2% to 5% (w/w) potassium or sodium phosphate, pH 6.5 to 7.8. In certain embodiments the dry formulation of the vaccine remains efficacious for at least 18 months at 27° C.

In even more particular embodiments, the present invention provides dry formulations of vaccines that comprise a live attenuated parvovirus, e.g., CPV, 23% to 49% (w/w) of sorbitol as the sugar alcohol, a combination of 8% to 17% (w/w) of glycine and 8% to 33% (w/w) of dextran as the bulking stabilizer, a combination of 3% to 18% (w/w) gelatin with 4% to 18% (w/w) of a proteolytic hydrolysate of whole casein as the protein stabilizer; and a buffer having a pH of 7.0 to 7.4. In certain embodiments of this type 25% to 36% (w/w) arginine is included as an amino acid stabilizer. In specific embodiments, the buffer is 0.5% to 2% (w/w) potassium or sodium phosphate, pH 7.0 to 7.4. In certain embodiments the dry formulation of the vaccine remains efficacious for at least 18 months at 27° C.

In particular embodiments, the canine parvovirus (CPV) is a canine parvovirus 2 (CPV-2). In another particular embodiment of this type, the canine parvovirus is a canine parvovirus 2a (CPV-2a). In yet another particular embodiment of this type, the canine parvovirus is a canine parvovirus 2b (CPV-2b). In still another particular embodiment of this type, the canine parvovirus is a canine parvovirus 2c (CPV-2c). In a specific embodiment of this type, the CPV-2c is ATCC accession No. PTA-13492. In yet another embodiment the canine parvovirus is a recombinant canine parvovirus that has been constructed to comprise a heterogenous CPV-2c/CPV-2 genome, i.e., the region encoding the capsid proteins is from a CPV-2c isolate and the region encoding the nonstructural proteins is from a CPV-2 isolate [see, U.S. 2012/0328652 A1, the contents of which are hereby incorporated by reference in their entireties, in which the nucleotide sequence encoding the capsid protein in the CPV-2 genome has been replaced by the nucleotide sequence encoding the capsid protein of a CPV-2c, thereby resulting in the heterogenous CPV-2c/CPV-2 genome].

As part of the process for making the stable dry formulations of live, attenuated vaccines of the present invention, the corresponding liquid vaccine formulations can be applied to a membrane, and/or frozen into beads, and/or frozen into containers such as vials, and/or spray dried, and/or spray freeze-dried, and/or induced to foam, and/or placed into a delayed-release implant.

The present invention further provides methods of aiding in the protection of an animal, (e.g., feline or canine) against a clinical disease that arises from an infection (e.g., by a feline or canine virus) comprising administering a reconstituted vaccine of the present invention to the animal. In certain embodiments the administration is performed mucosally. In other embodiments the administration is performed parenterally. In still other embodiments the administration is performed intradermally. In yet other embodiments the administration is performed transdermally. In more specific embodiments, a vaccine of the present invention is administered to the animal subcutaneously. In other specific embodiments, a vaccine of the present invention is administered to the animal intramuscularly. The present invention also includes the use of primary and/or booster vaccines.

In certain embodiments the therapeutically effective amount of a live attenuated virus is a therapeutically effective amount of a live attenuated canine virus. In specific embodiments of this type, the therapeutically effective amount of a live attenuated canine virus includes therapeutically effective amounts of live attenuated canine distemper virus, and/or a live attenuated canine adenovirus type 2, and/or a live attenuated canine parvovirus, and/or a live attenuated canine parainfluenza virus.

In particular embodiments, the animal subject is a canine and the method comprises administering to the canine a reconstituted room temperature stable vaccine of the present invention that comprises a live attenuated virus. In specific embodiments the room temperature stable vaccine comprises live attenuated canine distemper virus, live attenuated canine adenovirus type 2, and live attenuated canine parainfluenza virus. In certain embodiments of this type, the room temperature stable vaccine comprises live attenuated canine distemper virus, live attenuated canine adenovirus type 2, live attenuated canine parainfluenza virus, and either live attenuated canine influenza virus or live attenuated canine parvovirus or alternatively, both live attenuated canine influenza virus and live attenuated canine parvovirus.

Accordingly, the present invention further provides a reconstituted vaccine made up of any one or more of the dry formulations as provided herein and a pharmaceutically acceptable carrier. In particular embodiments, the present invention provides a multivalent vaccine made from the combination of a dry formulation of a trivalent CDV, CAV2, and CPI vaccine with a separate dry formulation of a monovalent CPV vaccine, and a pharmaceutically acceptable carrier.

Methods of making, and/or storing at room temperature (e.g., 22-27° C.), any and all of the room temperature stable dry formulations of the vaccines of the present invention are also provided. In certain embodiments the method comprises preparing a vaccine formulation by combining a therapeutically effective amount of a live attenuated feline or canine virus with 8% to 30% (w/v) of a non-reducing oligosaccharide, 0.1M to 0.5M of an amino acid stabilizer, 0.9% to 10% (w/v) of a protein stabilizer, and a buffer having a pH of 6.0 to 8.0. Generally next, but not always, the vaccine formulation is frozen and then dried under vacuum to make a room temperature stable dry formulation. The temperature inside the freeze dryer can be raised during this process to accelerate the removal of the moisture. Preferably the dry formulation of the vaccine remains efficacious for at least 18 months when stored at 27° C.

In particular embodiments of this type the vaccine formulation further comprises 1% to 6% (w/v) of a bulking stabilizer. In a more particular embodiment of this type the ratio of the bulking stabilizer to the non-reducing oligosaccharide is 0.05 to 0.40. In certain embodiments 0.5% to 5% (w/v) sorbitol is also included. In particular embodiments, the bulking stabilizer is mannitol. In certain embodiments the amino acid stabilizer is arginine. In others, the amino acid stabilizer is glutamate. In still other embodiments, the amino acid stabilizer is a combination of arginine and glutamate.

The methods of making any and all of the room temperature stable dry formulations of the vaccines of the present invention can include, prior to drying, applying the liquid vaccine formulation to a membrane, and/or freezing it into beads, and/or freezing it in vials, and/or spray drying, and/or spray freeze drying, and/or inducing it to foam.

In particular embodiments of the methods of making a room temperature stable vaccine the method comprises combining a therapeutically effective amount of a live attenuated virus with the non-reducing oligosaccharide that is a combination of 5% to 18% (w/v) of sucrose, and 5% to 18% (w/v) trehalose, 2% to 4% (w/v) of the bulking stabilizer, 0.1M to 0.3M of the amino acid stabilizer, and 1.5% to 6% (w/v) of the protein stabilizer. In more particular embodiments the ratio of the bulking stabilizer to the non-reducing oligosaccharide is 0.08 to 0.37. In certain embodiments the live attenuated virus is a live attenuated canine virus. In related embodiments the live attenuated virus is a live attenuated feline virus.

These and other aspects of the present invention will be better appreciated by reference to the following Detailed Description.

DETAILED DESCRIPTION OF THE INVENTION

The present invention provides safe and efficacious live attenuated virus vaccines and/or immunogenic compositions that can be stored as dry formulations at room temperature and still remain safe and efficacious for 12, or 18, or even 24 months or longer. Accordingly, one major advantage of the room temperature stable dry formulations of the vaccines of the present invention is that they eliminate the need of either a storage refrigerator or freezer. This significantly decreases the expense of storage, particularly in remote locations, and furthermore, eliminates the need to guess whether the vaccine has remained safe and efficacious after a storage refrigerator or freezer has malfunctioned.

Moreover, surprisingly the room temperature stable dry formulations of the live virus vaccines of the present invention can include live attenuated viruses of any type. Thus, the room temperature stable formulations of the live vaccines of the present invention can include both enveloped and non-enveloped viruses. In addition, the room temperature stable dry formulations of the live vaccines of the present invention can include live attenuated viruses having single-stranded RNA genomes, single-stranded DNA genomes, or double-stranded DNA genomes. In one aspect of the present invention the live virus vaccines of the present invention include live attenuated canine and/or feline viruses. The present invention further provides room temperature stable vaccines that are multivalent vaccines. Moreover, the room temperature stable vaccines of the present invention can further comprise a killed virus and/or a killed bacterium (e.g., a bacterin) and/or a sub-fraction of a bacterin, and/or subunit of the virus or bacterium (e.g., a protein antigen).

In addition, the room temperature stable live virus formulations of the present invention can comprise recombinant vectors, such as recombinant virus vectors (including recombinant baculoviruses) that are either alone, and/or with other such recombinant virus vectors, and/or with live attenuated viruses and/or in combination with killed bacteria and/or killed viruses, e.g., killed canine viruses. Such recombinant virus vectors can further encode one or more heterologous viral or bacterial antigens. A particular example of such a recombinant vector is a recombinant parainfluenza virus, e.g., canine parainfluenza virus. One recombinant parainfluenza virus vector is a recombinant parainfluenza Virus 5, which recently has been described by Li et al., [*J. of Virology* 87(10) 5985-5993 (2013); hereby incorporated by reference in its entirety]. Such recombinant virus vectors, e.g., a recombinant parainfluenza Virus 5 or recombinant canine parainfluenza virus vector, can encode a heterologous antigen from a canine virus, and/or a feline virus, and/or equine virus, and/or a human virus, and/or a simian virus, and/or a bovine virus, and/or an ovis virus, and/or a swine virus, and/or a poultry virus (e.g., a chicken virus). In particular embodiments, the room temperature stable dry formulations of the vaccines of the present invention comprise a recombinant parainfluenza virus (e.g., the recombinant parainfluenza Virus 5 or a recombinant canine parainfluenza virus) that encodes one or more antigens from one or more chicken viruses and/or bacteria that infect chickens.

In alternative embodiments of the present invention, the room temperature stable dry formulations of the vaccines of the present invention can comprise live attenuated bovine viruses and/or bacteria that infect cattle. In specific embodiments the room temperature stable vaccine comprises live attenuated BVDV1, live attenuated BVDV2, and live attenuated IBR virus. In other embodiments the room temperature stable vaccine comprises live attenuated BVDV1, live attenuated BVDV2, the live attenuated PI3 virus, and live attenuated BRSV. In still other embodiments, the room temperature stable vaccine comprises live attenuated BVDV1, live attenuated BVDV2, live attenuated PI3 virus, live attenuated IBR virus, and live attenuated BRSV. In yet other embodiments, the room temperature stable vaccine comprises live attenuated BVDV1, live attenuated BVDV2, live attenuated PI3 virus, live attenuated IBR virus, live attenuated BRSV, and live attenuated BRCV. Any of the room temperature stable vaccines of the present invention also can be combined with one or more attenuated or killed bacterial antigens such as *Pasteurella multocida, Mannheimia haemolytica, Histophilus somni*, and *Mycoplasma bovis* prior to administration. One such embodiment is the room temperature stable vaccine comprises live attenuated BVDV1, live attenuated BVDV2, live attenuated PI3 virus, live attenuated IBR virus, and live attenuated BRSV (plus or minus live attenuated BRCV) with live attenuated *Pasteurella multocida*, live attenuated *Mannheimia haemolytica*, and live attenuated *Histophilus somni*. In particular embodiments, the present invention provides methods comprising administering to a bovine a room temperature stable vaccine of the present invention that comprises a live attenuated bovine virus.

The room temperature stable dry formulations of the vaccines of the present invention alternatively can comprise live attenuated poultry viruses and/or bacteria that infect poultry. In certain embodiments the live attenuated poultry virus is infectious bronchitis virus (IBV). In other embodiments the live attenuated poultry virus is infectious bursal disease virus (IBDV). In yet embodiments the live attenuated poultry virus is Newcastle disease virus (NDV). In still other embodiments the live attenuated poultry virus is Infectious Laryngotracheitis (ILTV). In yet other embodiments the live attenuated poultry virus is avian metapneumovirus (aMPV). In still other embodiments the live attenuated poultry virus is Mareks disease virus (MDV). In yet other embodiments the live poultry virus is Herpes Virus of Turkeys (HVT). [HVT is not pathogenic in chickens.]

The live poultry viruses can also be recombinant vectors. This is especially true for HVT and the two other MDVs, i.e., MDV1 and MDV2. Recombinant HVT vectors are already commercially available that encode antigens from Newcastle Disease Virus or Infectious Laryngotracheitis. More recently, two unique recombinant HVT vectors have been described that encode antigens from both NDV and ILTV or from both NDV and IBDV [see, U.S. 2013/0101619 A1 and WO2013057235 A1, respectively, the contents of both of which are hereby incorporated by reference in their entireties]. The room temperature stable vaccines of the present invention can comprise any of these recombinant poultry virus vectors either individually or in any combination as described herein. Moreover, any of the room temperature stable vaccines of the present invention that comprise one or more live poultry virus vaccines can further comprise a killed virus and/or killed bacterium and/or a sub-fraction of a bacterin, or even a parasite such as a live *Eimeria* that is either attenuated or non-attenuated. In particular embodiments, the present invention provides methods comprising administering to poultry e.g., a chicken, a room temperature stable vaccine of the present invention that comprises a live attenuated poultry virus.

In yet another aspect a room temperature stable dry formulation of a vaccine of the present invention can comprise a live attenuated porcine virus. In certain embodiments the live attenuated porcine virus is transmissible gastroenteritis virus (TGE). In other embodiments the live attenuated porcine virus is porcine reproductive and respiratory syndrome virus (PRRS). In yet embodiments the live attenuated porcine virus is porcine epidemic diarrhea virus (PED). In still other embodiments the live attenuated porcine virus is swine influenza virus (SW). In yet other embodiments the live attenuated porcine virus is porcine rotavirus (PRV). In still other embodiments the live attenuated porcine virus is porcine parvo virus (PPV). In yet other embodiments, the live attenuated porcine virus is porcine pseudorabies virus (PPRV). In still other embodiments the live attenuated porcine virus is porcine circovirus (PCV).

The multivalent vaccines of the present invention can contain any combination of porcine viruses. In certain embodiments the multivalent vaccines of the present invention comprise both killed porcine viruses and live attenuated porcine viruses. In a particular embodiment of this type, the multivalent vaccine comprises a killed swine influenza virus SIV, a killed or subunit porcine circovirus (PCV) [which includes baculovirus-expressed PCV antigens, see, U.S. Pat. No. 8,008,001, the contents of which is hereby incorporated by reference], together with live attenuated transmissible gastroenteritis virus (TGE) and live attenuated porcine parvovirus (PPV). In a related embodiment, the multivalent vaccine comprises killed porcine circovirus antigen (PCV), killed swine influenza virus (SIV) of multiple serotypes, and killed, together with live attenuated transmissible gastroenteritis virus (TGE), and live attenuated porcine rotavirus (PRV). In particular embodiments, the present invention provides methods comprising administering to a porcine a room temperature stable vaccine of the present invention that comprises a live attenuated porine virus. In related embodiments, the multivalent vaccine comprises a live attenuated and/or inactivated and/or subunit porcine circovirus antigen (PCV), a live attenuated and/or inactivated and/or subunit porcine reproductive respiratory syndrome virus (PRRS) antigen, and/or an a live attenuated and/or inactivated or subunit porcine epidemic diarrhea virus (PED) antigen.

The room temperature stable live attenuated porcine virus vaccines of the present invention can further comprise a killed virus and/or a killed bacterium (e.g., a bacterin) and/or a sub-fraction of a bacterin. In particular embodiment sof this type, the multivalent vaccine comprises a *Clostridium perfringens* inactivated toxoid, pilus antigen extracted from *E. coli* bacteria from any of the following serotypes: K99, K88, 987P, or F41, together with live attenuated transmissible gastroenteritis virus (TGE) and live attenuated porcine parvovirus (PPV). In a related embodiment, the multivalent porcine vaccine comprises a killed or subunit porcine circovirus antigen (PCV), killed *Mycoplasma hyopneumonia* (M. hyo), an inactivated or live attenuated *Lawsonia intracellularis* bacterin, together with a live attenuated and/or inactivated porcine reproductive respiratory syndrome virus (PRRS) and/or live attenuated or inactivated porcine epidemic diarrhea (PED) virus.

The room temperature stable dry formulations of the vaccines of the present invention include at least one sugar stabilizer, at least one protein stabilizer, and at least one buffer to maintain the liquid form of the vaccine at a pH of pH 5.5 to 8.5. At least one bulking stabilizer can also be added. The room temperature stable vaccines of the present invention therefore, are stored as dried formulations. Such dried formulations can be prepared by methods including freeze-drying in beads, e.g., such as spheres known as a lyospheres and/or sphereons produced by a method previously described [see e.g., WO 2010/125084; US 2012/0049412 A1; and US 2014/0017318, the contents of all of which are hereby incorporated by reference in their entireties] or as a cake, e.g., in vials, or dried on a solid matrix, e.g., on a membrane or filter, or alternatively, as dried as a powder, or spray dried, or spray freeze dried, or induced to a foam.

The active immunogenic fractions of the monovalent or multivalent vaccines can comprise one or more viruses and/or bacteria. Accordingly, the room temperature stable vaccines of the present invention may be freeze-dried (or otherwise reduced in liquid volume) for storage, and then reconstituted in a liquid carrier, e.g., with a pharmaceutically acceptable carrier such as a vaccine-grade water or other diluent before or at the time of administration. In particular embodiments the diluent comprises one or more other viral and/or bacterial antigens. Alternatively, the room temperature stable vaccines of the present invention can be injected as a solid, e.g., when the solid is a powder and the injector is a needleless powder injecter, such as PowderJect®.

The use of singular terms for convenience in the description is in no way intended to be so limiting. Thus, for example, reference to a "sugar stabilizer" includes reference to one or more of such sugar stabilizers, unless otherwise specified. The use of plural terms is also not intended to be limiting, unless otherwise specified.

Similarly, a chemical compound that can be referred to as an acid or its corresponding base when denoted herein as either is intended to mean either form of the compound, unless otherwise specified. Thus, the use of the term glutamic acid is meant to include glutamate and vice versa.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, an "efficacious" vaccine retains sufficient titer for a given antigen to be compliant with the regulatory requirements for that antigen for the jurisdiction where the vaccine is administered, e.g., administration of an animal vaccine in the United States is governed by the United States Department of Agriculture (USDA).

As used herein, a "multivalent vaccine" is a vaccine that comprises two or more different antigens. In a particular embodiment of this type, the multivalent vaccine stimulates the immune system of the recipient against two or more different pathogens.

As used herein, a "room temperature stable" dry formulation of a vaccine is a dry formulation of a vaccine (including a multivalent vaccine) that remains efficacious for at least one year when stored at 27° C. In particular embodiments a room temperature stable dry formulation of a vaccine remains efficacious when stored at 27° C. for at least 1.5 years. In more particular embodiments a room temperature stable dry formulation of a vaccine remains efficacious when stored at 27° C. for at least 2 years. In still more particular embodiments a room temperature stable dry formulation of a vaccine remains efficacious when stored at 27° C. for at least 2.5 to 3 years.

As used herein a "dry formulation" of a vaccine is prepared by removing the liquid of a vaccine that has been formulated in a solution. The removal of the liquid can be accomplished by e.g., evaporation, such as by the application of the liquid vaccine to a solid substrate and evaporation of the liquid and/or by sublimation such as by lyophilization (freeze-drying). The vaccines of the present invention are stored as dried formulations generally with 0.5% to 10.0% (w/w) residual moisture content (RMC). The dry formulations can be reconstituted in a pharmaceutically acceptable carrier prior to administration. In particular embodiments the vaccines of the present invention are stored as dried formulations comprising 0.5% to 5% (w/w) residual moisture content. In more particular embodiments the vaccines of the present invention are stored as dried formulations comprising 0.5% to 3% (w/w) residual moisture content.

Because the vaccines of the present invention are stored as dry formulations, a "vaccine" of the present invention also refers to the formulations comprising one or more antigens that are stored as dry formulations. As stated above some time prior to administration, these dried formulations can be combined with a pharmaceutically acceptable carrier. Antigens for a multivalent vaccine can be stored in the same dry formulation or in separate dry formulations. Accordingly for certain multivalent vaccines, individual vaccine antigens are stored separately as single dry formulations and then then prior to administration are combined together with a pharmaceutically acceptable carrier to form the multivalent vaccine. Alternatively, multiple vaccine antigens can be combined and stored as a single dry formulation, and then prior to administration can be mixed together with a pharmaceutically acceptable carrier and one or more other vaccine antigens that had been stored in one or more separate dry formulation(s).

As used herein, the term "carrier" refers to a diluent, adjuvant, excipient, or vehicle with which the compound is administered.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient, e.g., a pharmaceutically acceptable carrier. Pharmaceutically acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions. In particular embodiments the pharmaceutically acceptable carrier is and/or contains an adjuvant. In certain embodiments, a pharmaceutically acceptable carrier can further comprise one or more vaccine antigens which prior to administration, can be combined with a dry formulation of a vaccine of the present invention.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, the term "therapeutically effective amount" is an amount of a given antigen, e.g., live attenuated virus, which is sufficient to provide protection to and/or aid in the protection from the pathogen that the antigen is being administered to protect against, when provided in a single administration and/or when intended, provided as an initial administration with one or more subsequent booster administration(s).

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein the terms "livestock" and "livestock animal" includes cattle, pigs, and poultry. As used herein the terms "bovine" and "cattle" are used interchangeably, unless otherwise noted. Similarly, the terms "porcine", "swine", and "pig" are used interchangeably, unless otherwise noted. As used herein the terms "avian" and "fowl" are used interchangeably with both terms intended to include poultry. As used herein the term "poultry" can include chickens, turkeys, ducks, geese, quail, and pheasants.

As used herein the term "companion animal" includes canines, felines, and equines.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein, the term "canine" includes all domestic dogs, Canis lupus familiaris or Canis familiaris, unless otherwise indicated.

Canine parvovirus "CPV" was first isolated in 1978 and was named CPV-2 to distinguish it from canine parvovirus Minute virus (CMV or CPV-1). Approximately a year after the initial isolation of CPV-2, a genetic variant, CPV-2a, was identified. In the mid-1980's, a second genetic variant, CPV-2b, was identified. CPV-2a and CPV-2b soon completely displaced CPV-2. Today, CPV-2a is no longer detected in the United States [Parrish and Kawaoka, *Annu Rev. Microbial.*, 59:553-586 (2005)]. A fourth CPV variant in this family, CPV-2c, was first described in 2000 [see, U.S. Pat. Nos. 8,227,593; 8,258,274; Hong et al., *J. Vet. Diagn. Invest.* (5):535-9 (2007)]. U.S. provisional applications 61/739,067 filed Dec. 19, 2012, and 61/778,751 filed Mar. 16, 2013, the contents of both of which are hereby incorporated by reference in their entireties, describes a specific attenuated CPV-2c isolate (ATCC accession No. PTA-13492) that was deposited on Jan. 24, 2013 with the American Type Culture Collection (ATCC) 10801 University Boulevard, Manassas, Va. 20110-2209, U.S.A., under conditions that satisfy the requirements of the Budapest Treaty on the International Recognition of the Deposit of Microorganisms for the Purposes of Patent Procedure. In addition, a recombinant canine parvovirus has been constructed that comprises a heterogenous CPV-2c/CPV-2 genome, i.e., the region encoding the capsid proteins is from a CPV-2c isolate and the region encoding the nonstructural proteins is from a CPV-2 isolate [WO2011107534 (A1); US 20120328652; WO2012007589 (A1) the contents of which are hereby incorporated by reference in their entireties, in which the nucleotide sequence encoding the capsid protein in the CPV-2 genome has been replaced by the nucleotide sequence encoding the capsid protein of a CPV-2c, thereby resulting in the heterogenous CPV-2c/CPV-2 genome]. As used herein, a vaccine of the present invention that comprises "canine parvovirus" can comprise one or more of these CPV types/variants/isolates, including the recently constructed recombinant canine parvovirus that comprises the heterogenous CPV-2c/CPV-2 genome.

As used herein a "non-reducing oligosaccharide" is a carbohydrate consisting of two to ten monosaccharide residues joined through glycosidic linkages, and which in basic aqueous medium do not generate any compounds containing an aldehyde group. Examples of non-reducing oligosaccharides of the present invention include sucrose, trehalose, and raffinose.

As used herein a "sugar stabilizer" is a non-reducing oligosaccharide (e.g., see above) or a "sugar alcohol"/polyol (e.g., sorbitol, mannitol, arabitol, inositol, maltitol).

As used herein a "bulking stabilizer" is a compound that aids in the stabilization of a vaccine at elevated temperatures, i.e., 25°-30° C. or higher. Examples of such bulking stabilizers are mannitol, glycine, dextran, maltodextrin, polyvinylpyrrolidone, hydroxyethyl starch, polyethylene glycol (PEG, with a molecular weight range from 400 daltons to 20 kilodaltons), or any combination thereof. In particular embodiments, the "bulking stabilizer" is mannitol.

As used herein, unless otherwise specifically stated to the contrary, the percent (%) of a solid additive, e.g., non-reducing oligosaccharide or protein stabilizer, in a vaccine can be given as either weight/weight (w/w) and/or based on a 1% solution being 1 g of solid/100 ml of vaccine volume, weight/volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As provided herein, a ratio of two reagents in a given formulation, e.g., the ratio of the bulking stabilizer to the non-reducing oligosaccharide and/or the sugar alcohol, is based on the reagents having the identical units, e.g., (w/w).

As used herein an "amino acid stabilizer" is a charged amino acid, i.e., arginine, lysine, glutamic acid, and aspartic acid.

As used herein a "protein stabilizer" can be an intact protein and/or a protein hydrolysate. In particular embodiments the "protein stabilizer" of the present invention is either a hydrolyzed casein or a collagen/collagen derivative, such as gelatin. The hydrolysate of whole casein that can be used in the room temperature stable vaccines of the present invention can be obtained by a number of procedures including e.g., as an acid hydrolysate or an enzymatic hydrolysate.

Such hydrolysates contain in the form of mixed amino acids and peptides all amino acids originally present in casein. One pancreatic hydrolysate of whole casein that can be used in the room temperature stable vaccines of the present invention is sold as CASEIN HYDROLYSATE ENZYMATIC® by MP Biomedicals. Comparable products are sold under the name of NZ-AMINE®, NZ-AMINE® A, NZ-AMINE® AS, NZ-AMINE® B, and Tryptone by Sigma-Aldrich.

Because the room temperature stable vaccines of the present invention ideally range in pH from pH 5.5 to pH 8.5, the room temperature stable vaccines of the present invention comprise a buffering agent, i.e., a buffer. Buffers for use in the room temperature stable vaccines of the present invention include but are not limited to: histidine, potassium and/or sodium phosposphate, sodium or potassium pyrophosphate, imidazole, Tris, Tris-Histidine, BIS-Tris, and the Good buffers: BIS-Tris-Propane (BTP), PIPES, ACES, MOPS, MOPSO, BES, TES, tricine, glycylglycine, and HEPES. The buffers can be brought to the desired pH with the use of any suitable counterion.

As used herein, when a pH of a buffer in a dry formulation of a vaccine of the present invention is provided, that pH is the pH of the vaccine formulation comprising the buffer prior to removing essentially all of the liquid from the vaccine (i.e., drying) to make it a dry formulation. As used herein, unless otherwise specifically stated to the contrary, the pH value provided is the pH value determined/measured at 25° C.

Multivalent Vaccines: The present invention provides room temperature stable multivalent vaccines comprising human, livestock, or companion animal viruses as detailed herein. Examples of room temperature stable multivalent canine vaccines of the present invention, include but are in no way limited to: two or more of the following live attenuated viruses or recombinant vectors: canine distemper virus, canine adenovirus type 2, canine parvovirus, canine parainfluenza virus, canine influenza virus, canine pneumovirus, canine coronavirus, canine herpes virus, infectious canine hepatitis virus, canine minute virus, rabies virus, pseudorabies virus, a recombinant virus vector, e.g., a recombinant canine or feline virus vector, that encodes and expresses a heterologous antigen from a canine pathogen, and/or a feline pathogen.

In addition, the room temperature stable canine vaccines of the present invention can further contain and/or be subsequently combined with one or more attenuated or killed antigens such as *Bordetella bronchiseptica*, a *Mycoplasma* species, *Ehrlichia canis*, an *Anaplasma* species, *Leptospira canicola, Leptospira grippotyphosa, Leptospira hardjo, Leptospira icterohaemorrhagiae, Leptospira pomona, Leptospira interrogans, Leptospira autmnalis*, or *Leptospira Bratislava*; or killed canine influenza virus, or killed canine coronavirus prior to administration.

The present invention further provides room temperature stable multivalent vaccines comprising recombinant virus vectors, such as a recombinant canine parainfluenza virus vector, that encode a heterologous antigen obtained from a human pathogen, and/or a simian pathogen, and/or a bovine pathogen, and/or an ovis pathogen, and/or a swine pathogen, and/or a poultry pathogen (e.g., a chicken virus).

Similarly, a room temperature stable multivalent feline vaccine of the present invention can comprise two or more of the following live attenuated feline viruses: a feline herpesvirus, feline calicivirus, feline pneumovirus, feline parvovirus, feline leukemia virus, feline infectious peritonitis virus, feline immunodeficiency virus, borna disease virus, feline influenza virus, and avian influenza. Such room temperature stable vaccines can further contain and/or be subsequently combined with attenuated or killed *Chlamydophila felis* and/or *Bartonella* spp. (e.g., *B. henselae*) prior to administration.

The room temperature stable vaccines and multivalent vaccines of the present invention are stored as dry formulations and therefore, individual antigens can be packaged and stored either separately or in any combination prior to mixing with a pharmaceutically acceptable carrier and administering to the animal recipient. In one such example, a multivalent vaccine comprising a canine distemper virus antigen, a canine parainfluenza virus, and a canine adenovirus type 2 antigen is stored in a single dried formulation and a canine parvovirus antigen is stored in a second dried formulation. Prior to administering to the canine recipient, the two dried formulations are combined with a carrier to make a multivalent canine distemper virus, canine parainfluenza virus, canine adenovirus type 2, and canine parvovirus vaccine.

Vaccine Administration: Following being mixed with a carrier the room temperature stable vaccines of the present invention may be administered by any conventional means, for example, by systemic administration, or by parenteral administration such as, without limitation, subcutaneous or intramuscular administration. Following being mixed with a carrier the room temperature stable vaccines of the present invention also may be administered by mucosal administration, such as by intranasal, oral, intratracheal, rectal, and/or ocular administration. Alternatively, the vaccines may be administered via a skin patch, scarification, or topical administration. It is contemplated that a room temperature stable vaccine of the present invention also may be administered via the drinking water and/or food of the recipient. It is further contemplated that such vaccines may be administered in the form of a treat or toy.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

The immunogenicity level may be determined experimentally by challenge dose titration study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the species or breed (e.g., of a canine or feline), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL, and 1.0 to 2.0 mL for intramuscular or subcutaneous administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered. Subsequent administrations of the vaccine also may be made on an annual (1-year) or bi-annual (2-year) basis, regardless as to whether a booster was administered or not.

The present invention may be better understood by reference to the following non-limiting Examples, which are provided as exemplary of the invention. The following Examples are presented in order to more fully illustrate embodiments of the invention. They should in no way be construed, however, as limiting the broad scope of the invention.

EXAMPLES

Materials and Methods

Materials: Minimum ACS grade sucrose and sorbitol are purchased from Fisher Scientific. Molecular grade L-arginine hydrochloride, L-methionine, L-histidine, mannitol, magnesium sulfate, ectoine, hydroxyectoine, glycine, and sodium chloride with a purity of more than 98% are purchased from Sigma. Dextran with an average molecular weight 70,000 at a purity >95% is purchased from Sigma. Molecular biology grade 1.0M Tris (pH 8.0) and EDTA (pH 8.0) solutions are purchased from Sigma. 20% Gelatin bloom 250 solution and NZ Amine AS solution were prepared from the best available commercial suppliers.

Stock Solution Preparation: The following solutions have been prepared and sterilized by 0.2 μm filtration: 80% sucrose, 70% sorbitol, 1.0M L-arginine (pH 7.2), 5% L-methionine, and 5 mM dextran sulfate. Bulk antigens CDV, CAV2, CPV, and CPI having titers between 6.5 to 9.5 were frozen at −80° C. to be thawed immediately before blending.

Vaccine Blending, Filling, and Drying: Virus antigens and stabilizers are blended to the final concentration of each component as listed in the formulation table. Deionized water is used to make the solution to the target volume. All the components in the vaccine blends are mixed thoroughly by stirring for at least 10 minutes on a stirring plate. For vaccines dried in vials, the blend is dispensed into 2.2 cc glass vials at 0.5 mL per vial, then freeze-dried in a lyophilizer using a drying cycle developed as shown in Table 4. For vaccines dried in beads (e.g., lyospheres/sphereons), the blend was dispensed on ultra-cold stainless steel molds at 100 uL per drop to obtain a frozen spherical beads. The frozen beads were transferred to a tray and freeze-dried in the lyophilizer using the optimized drying cycle as shown in Table 5. For vaccines dried on membranes, the vaccine blend is dispensed on a membrane and then the membrane is dried in a chamber with vacuum controlled at 100 to 1000 mTorr for around 16 hours at 25° C.

Stability Testing at Accelerated Temperature and Real-Time:

Accelerated stability testing at 45° C. and 37° C. are used to screen different formulations. The leading formulations are monitored in the long-term real time stability testing at 27° C., when it is desired. At the designated time point, 3 samples from each formulation were retrieved and the titer of each antigen were measured by a cell culture based titration assay and reported as a median tissue culture infective dose ($TCID_{50}$) and/or as a 50% fluorescent antibody infective dose ($FAID_{50}$).

Analytical Methods:

CPI Potency: Dilutions of virus samples are inoculated onto dog kidney (DK) cells. After 4-6 days, monolayers are fixed and stained with fluorescein-conjugated CPI antiserum, and the virus titer is calculated by the Spearman-Karber Method [Cunningham, C. H. *A Laboratory Guide in Virology,* 7$^{th}$ edition, Burgess Publishing Co., Minneapolis, Minn. (1973); Kaplan, M. M. and Koprowski, H., *Laboratory Techniques in Rabies, World Health Organization, Switzerland*, (1973)].

CDV Potency: Dilutions of virus samples were inoculated onto Vero cells. After 5-7 days, monolayers are observed for cytopathic effect, and the virus titer is calculated by the Spearman-Karber Method, as cited above.

CAV2 Potency: Dilutions of virus samples were inoculated onto DK cells. After 7 days, monolayers are observed for cytopathic effect, and the virus titer is calculated by the Spearman-Karber Method, as cited above.

CPV Potency: Dilutions of virus samples were inoculated onto DK cells. After 3 days, monolayers are stained with fluorescein-conjugated CPV antiserum, and the virus titer is calculated by the Spearman-Karber Method, as cited above.

Moisture and Thermal Analysis of the Dried Vaccine: Moisture of the freeze-dried vaccine in vials or in beads was determined using the traditional vacuum oven gravimetric method or the Karl-Fischer method. [The residual moisture content (RMC) of the freeze-dried samples was found to vary from 0.5% to 3% (w/w).] The glass transition temperatures of the freeze-dried beads or cakes in vials were determined on a differential scanning calorimetry (DSC) instrument. Unless otherwise noted, the RMC is provided as a percent (w/w) in the freeze-dried formulations.

Example 1

Preparation of Stabilizers

The final target concentration (w/w) of each component in the final dried vaccine of each formulation is shown in Tables 1a and 2a. The final concentration of each component in the vaccine blend of each formulation is shown in Tables 1b and 2b. For vaccine dried as beads (e.g., lyospheres/sphereons) in a plastic tray, the volume of each dose of vaccine is 100 μL or 250 μL. For vaccines dried as a cake in a glass vial, the dose volume is 250 μL, or 500 μL, or 1000 μL. For stabilizers in dried vaccines shown in Table 1a and 2a, all the concentration units are weight by weight (w/w) except the total dose vaccine weight is in mg. For stabilizers in vaccine blends shown in Table 1b and 2b: the concentration for the sugar and the protein are the percentage of weight by volume (w/v), the concentration for amino acids, cations, and buffers are molar (M) or millimolar (mM), the concentration for ectoine and hydroxyectoine are weight by volume (w/v). All concentrations shown in Tables 1b and 2b are the final concentration in the vaccine blend with virus antigens. The L-arginine in formulations SP33 and SP34 is the phosphate or acetate salt, respectively. All other L-arginine formulations are the chloride salt. The pH is the final pH of the vaccine blend with the virus antigens. All buffers in the formulation have a final concentration of 10 mM. KPO4 is potassium phosphate buffer comprising monobasic and dibasic potassium phosphate with the target pH of 7.2. The stabilizers listed in Tables 1b and 2b are thoroughly mixed with the appropriate amount of water, then the virus antigens are added and thoroughly mixed before the ensuing vaccine blend is dispensed, frozen, and freeze-dried either into beads or in vials.

Example 2

Correlation of 27° C. Stability with 37° C. and 45° C. Studies

Accelerated stability testing at elevated temperature is used to screen different stabilizers. Elevated temperatures of 45° C. and 37° C. are used for accelerated stability testing in these studies. The real time long-term stability testing is carried out at 27° C. To investigate whether the accelerated stability testing at 45° C. and 37° C. can be used to screen different stabilizers or formulations, the stability profile of at least three formulations for each virus at 45° C., 37° C., and 27° C. were compared (Table 3). Relative virus stability in different formulations is ranked based on virus titer at each time point and also the overall trend of titer loss. Similar ranking is used for the same formulations at different temperatures. As seen in Table 3, there is a tight correlation between accelerated and real time stability testing among all 3 temperatures. The relative stability performance at 45° C., 37° C., and 27° C. is always consistent for all four viruses in different formulations. For most of the formulations, the ranking is consistent among all three temperatures. Therefore, the data indicate that 45° C. and 37° C. can be a reliable accelerated formulation screening method, particularly to distinguish the best and the worst formulations in the group. For some formulations with very similar stability profiles at elevated temperatures of 45° C. and 37° C., it is not as easy to predict which one will give better stability at 27° C. (real time). In the formulation screening for DHPPi (CDV, CAV2, CPV, and CPI), accelerated stability testing at 45° C. and 37° C. is used to screen different stabilizers and excipients to identify the leading formulations. The leading formulations can then be confirmed with long-term real time stability testing at 27° C., when desired.

Example 3

Drying Process for Virus in Different Formulations

After the stabilizers and virus antigens are mixed thoroughly, the glass transition temperature (Tg) prime of the vaccine blend were measured on a differential scanning calorimeter (Perkin Elmer). All the formulations in Tables 1 and 2 have a Tg prime higher than −40° C. Based on these results, the drying cycle in Tables 4 and 5 is used to dry the frozen vaccine beads and liquid in vials, respectively.

To prepare vaccines in dry beads, the frozen vaccine beads with 100 μL per bead are first prepared by dropping the vaccine blend to wells in pre-chilled stainless steel plates (−110° C. to −130° C.). The frozen beads were collected in a tray and stored at −80° C. until drying in the lyophilizer. Immediately before freeze-drying of the vaccine beads, the shelf of the freeze-drier is pre-chilled to −20° C. and the vaccine beads in the trays are quickly loaded on the shelf. After freeze-drying with a drying cycle shown in Table 4, the vacuum is released using dry argon or dry nitrogen gas. The dried trays of beads are sealed in foil pouches with dry argon or nitrogen.

To prepare the vaccine as cakes in vials, the vaccine blend was dispensed into 2.2 cc glass vials at 250 μL per vial. The filled vial was then stoppered and transferred to the 4° C. pre-chilled shelf in the freeze-drier. The drying cycle in Table 5 was used to freeze-dry the vaccines in vials. After freeze-drying, the vacuum was released and the vials were filled with dry argon or nitrogen gas. Then the vials were fully sealed with a rubber stopper and then further capped with a crimper.

Example 4

Stability Results of Freeze-Dried CDV, CAV2, CPI, and CPV

For viruses dried in beads, the freeze-dried beads with antigens are packed into containers in a glove box with dry nitrogen [<1.0% Relative Humidity (RH)] and then stability tested at different temperatures. For samples dried as a cake in vials, the sealed vial is placed into a storage box and then stability tested in incubators at different temperatures. At different time points, the samples are retrieved from the incubator and the potency of each vaccine is titrated using the cell culture based titration assays.

At each time point, at least three vials of same formulation were retrieved and reconstituted with 1 mL PBS per vial for a potency assay. The potency of the viruses was determined using cell culture based $TCID_{50}$ and/or $FAID_{50}$ methodology. The formulation screening are carried out step by step in different studies. Each study includes at least one baseline formulation to compare with other studies. Within each study, different formulations were scored with one or more "+" and then ranked based on relative stability data at multiple time points. The greater the number of +'s, the better is the relative stability of the particular virus tested in the sample.

For most of the SPxx formulations, the physical stability of the beads (e.g. lyospheres/sphereons) are acceptable without changes in the bead or the cake appearance during long-term storage, so no ranking of physical stability is listed. For the SPCPVxx formulations, the physical stability varied depending on components in the formulation. The physical stability of the dried vaccine was ranked by Tg and by visually inspecting the physical appearance.

Table 6 shows the stability of the four viruses at 27° C. in different formulations and their projected shelf life at 27° C. In these tests, the target antigen input titer [$Log_{10}$ ($TCID_{50}$)] for CDV, CPI, CAV2, and CPV were 7.0, 7.0, 4.0, and 5.0, respectively. The minimum titer at expiration for each antigen was set as 4.7, 5.0, 3.3, and 4.5 for CDV, CPI, CAV2, and CPV, respectively. The estimated shelf life for DHPPi virus in different formulations is calculated from the trend of titer change at multiple time points during stability studies. The estimated shelf life for CPI is based on the minimum titer at expiration which is 5.0 and the input of antigen for CPI is 0.5 log higher. In other studies, several leading formulations showed improved stability at 45° C. and 37° C. over the formulations listed in Table 6. These leading formulations can be re-tested by long-term real time stability testing at 27° C. The data shown in Table 6 indicates that using the current vaccine manufacture specifications, the SP10 formulation minimally can provide 18 months or longer shelf life at 27° C. for CDV, CAV2, and CPI (with the CPI antigen input 0.5 log higher).

Table 7 shows several leading formulations identified using the 45° C. accelerated stability testing. CDV, CAV2, CPI, and CPV viruses are blended in these formulations and then freeze-dried into beads. The beads were sealed in vials with dry nitrogen and then put on stability testing at 45° C. Similarly, the stability ranking is based on the titer at each time point and the rate of titer change along the time course.

As shown in the Table 7, formulation SP43 and SP44 provide significantly better stability for CDV and CPI than SP10. There is more than a half log improvement at weeks 1, 2 and 4 for both CDV and CPI in SP44 relative to that in SP10. Similarly, SP44 also provides significantly better stability for CAV2 than SP10. The stability improvements for formulation SP44 relative to SP10 can be extrapolated to yield a stable CDV, CAV2, and CPI vaccine (DHPi vaccine) that has a shelf life of 24 months or longer at 27° C., when the data obtained from the accelerated studies at 45° C. for SP44 is compared to that obtained at 27° C. for SP10.

The effects of stabilizers or excipients on the virus stability have been thoroughly evaluated during the formulation screening of CDV, CPI, CAV2, and CPV. Several screening examples are listed in Tables 8-13.

The effect of buffer and pH on the virus stability is shown in Table 8. In the study described in Table 8, vaccines were freeze-dried as cakes in vials. All four viruses were blended in the formulations as in the table, filled in glass vials, and then freeze-dried in a lyophilizer as described in methods using drying cycle shown in Table 5. Except for the difference in buffer [potassium phosphate buffer (KPO4), histidine, bis-tris propane buffer (BTP), and MOPS (3-(N-morpholino) propanesulfonic acid)] and the pH listed, all formulations in this study contain 4% mannitol, 5% sucrose, 0.8% gelatin, 1.0% NZ Amine, and 2 mM MgSO4. All formulations in this study also contain 10 mM buffer with a final pH listed in the table. The stability data at 45° C. and 37° C. for each virus are used to rank the formulations.

The data provided in Table 8 indicate that CDV, CPI, and CAV2 have a higher stability at lower pH (6.5) than at neutral or higher pH, whereas CPV has a higher stability at neutral to higher pH (7.6). CDV and CPI are more stable in KPO4 or histidine than the other two buffers tested, whereas the stability of CAV2 and CPV appears to be less dependent on the buffer used.

The effect of sugar concentration and combination on the stability of the viruses was investigated as shown in Tables 9a and 9b. The sugar concentrations are listed in Table 9a and the stability of viruses in these formulations at 45° C. and 37° C. are listed in Table 9b. In this study, all formulations have the same virus bulk antigen input and the viruses in these formulations were freeze-dried into beads. The relative stability ranking is based on stability data at both 45° C. and 37° C. and at multiple time points for each virus in the different formulations. The data in Tables 9a and 9b suggest that the stability of CDV, CPI, and CAV2 has a strong dependency on sugar concentration, with higher stability of viruses at higher concentration sugar in the range of 4-30%. The data also suggest that combination of sucrose and trehalose (Suc+TrH) appears to work better than either sucrose or trehalose alone.

The effect of L-arginine concentration on the stability of the viruses also was investigated (Table 10). Formulations SP02B, SP26, and SP27 differ by only the concentration of L-arginine hydrochloride. [For some data points the data is not available due to assay invalidity (n/a)]. Based on data obtained at 45° C. and 37° C., the stability of CDV, CPI, and CAV2 appears to depend on the arginine concentration, with higher concentrations of arginine being more stable (Table 10).

The effect of different arginine salts or concentrations of arginine in combination with glutamic acid were further investigated (Tables 11a and 11b). Table 11a shows the concentration and salt of arginine, and the concentration glutamic acid in each formulation and the corresponding onset of Tg of dried vaccine. All formulations are the same, except the aforementioned differences in arginine and glutamic acid. L-arginine was adjusted to pH 7.2 with different acids to produce the different arginine salts. The onset Tg is the onset glass transition temperature of the freeze-dried vaccine beads in the formulation. The onset Tg is determined by differential scanning calorimetry and is the average of at least 3 replicates. The stability data at 45° C. and 37° C. of the formulations listed in Table 11a is shown in Table 11b. The relative stability is also ranked and listed in Table 11b. As shown in Table 11a and 11b, different L-arginine salts can have different stability effects. Although arginine phosphate in formulation SP33 provides a much higher Tg, the stability of all 3 viruses decreased relative to the other arginine salts. Combining 0.15M arginine chloride with 0.15M monobasic sodium glutamic acid in formulation SP35 slightly improved the stability of all three viruses relative to that found in SP10.

Ectoine and hydroxyectoine are natural compounds found in halophilic microorganisms. Both are compatible solutes which serve as a protective substance by acting as an osmolyte and thus help organisms survive extreme osmotic stress conferring resistance towards salt and temperature stress. Both ectoine and hydroxyectoine have been shown to be potent stabilizers of proteins, as well as many other biologicals. Therefore, their stabilizing effect on the stability of CDV, CPI and CAV2 was tested. Formulations SP39 and SP40 are identical to formulation SP10 except, in addition they contain either ectoine or hydroxyectoine, respectively (Table 13). Stability data at three storage temperatures were used to evaluate their stabilizing effects. The vaccine blend containing these 3 virus fractions were freeze-dried in beads using the same drying cycle.

The stability ranking is based on stability data from the 3 temperatures (at 45° C., 37° C., and 27° C.). The stability data and stability ranking in Table 13 indicate that both ectoine and hydroxyectoine can improve the stability of CDV and CPI at 37° C. and 27° C., although the stabilizing effects at 45° C. is not that significant. The stabilizing effect of ectoine and hydroxyectoine on CAV2 is difficult to determine due to its low degradation curve.

Example 5

Stability Results of Freeze Dried CPV

The stability of monovalent CPV in different formulations also has been evaluated. Although CPV can be included together with the other three canine viruses in a viable room temperature stable formulation, e.g., SPCPV-02 and SPCPV-03 formulations can provide around 18 months of shelf life at 27° C. for CPV, of the four different canine viruses tested, CPV differs the most with respect to its optimal room temperature stability.

Accordingly, CPV has a different preference towards sugars than CDV, CPI, or CAV2, e.g., being more stable with a sugar alcohol such as sorbitol, than a reducing sugar. However, even in the presence of sorbitol, the physical stability of either the freeze-dried beads or cakes can sometimes lead to shrinkage or collapse of the dried beads during storage. Therefore, both the stability of the potency and the physical stability of dried CPV formulations were monitored during formulation screening. Notably, the screening of monovalent CPV vaccine formulations proved to be a model study for achieving a vaccine product that balances virus potency stability with dry product physical stability.

Table 14 shows the stability data of CPV at 45° C., 37° C., and 27° C. in five different formulations. Monovalent CPV is blended into these formulations and then freeze-dried as 100 uL size beads. All formulations in this study contained 10 mM KPO4 at pH 7.2 as buffer, and 2% Dextran 70 k and 2% Glycine as bulking stabilizers. The sorbitol concentration (w/v) of each formulation is shown in the table. All formulations also contained stabilizing proteins “GN” (Gelatin and NZ-Amine). 1×GN is: 0.8% Gelatin and 1.0% NZ Amine; whereas 2.5×GN is: 2.5% Gelatin and 2.5% NZ Amine. The potency stability ranking is based on the virus titer change at 45° C., 37° C., and 27° C. The physical stability ranking is based on the glass transition temperature (Tg) and physical structure appearance of the freeze-dried beads after freeze-drying and during the stability study. Higher Tg and a stronger tendency to maintain the beads’ physical structure yields a higher score in physical stability.

The stability data in Table 14 indicate that a higher concentration of sorbitol benefits the CPV potency stability, but lessens the vaccines physical stability; whereas a higher protein concentration is beneficial to the physical stability. In addition, the inclusion of L-arginine had no negative effects on the CPV stability.

The effect of dextran and different concentrations of sorbitol was further evaluated in a study summarized in Table 15. All of the formulations in Table 15 contain 2% Glycine, 2.5% Gelatin, 2.5% NZ Amine, and 10 mM KPO4 buffer at pH 7.2. Additionally, all formulations contain sorbitol and dextran 70 k. The monovalent CPV is blended into these formulations and then freeze-dried as 100 uL size beads. The potency and physical stability of these formulations are ranked similarly as in the study of Table 15. The data in Table 15 indicates that the higher concentration of Dextran 70 k is beneficial to freeze-dried CPV beads physical stability, but impairs the potency stability at 6%. Meanwhile, higher concentration of sorbitol is beneficial to potency stability but needs medium concentration of dextran 70 k to maintain its structure. The data in this study suggest that an optimal combination of sorbitol and dextran 70 k are required for an optimal freeze-dried CPV vaccine having both high potency and high physical stability.

Example 6

Effects of Different Drying Format on Virus Stability

To investigate whether the vaccines dried in different formats have different stability profiles, the viruses in the same formulation were dried either as a cake in a vial or as beads in a tray, and then their stability was compared. Table 16 shows the stability testing results of CDV, CAV2, and CPI in beads in SP02B and in a cake in FDIV-03. (SP02B and FDIV-03 are actually the same formulation). As seen from Table 16, the stability of CDV, CPI, and CAV2 in a vial was equivalent (or slightly better than) to that observed in beads. The data in this study suggest that the optimal formulations identified in beads can also be used for the virus vaccines dried as cakes in vials.

TABLE 1a

Stabilizers and Excipients (w/w) in the Dried Vaccine Products Containing CDV, CAV2, CPV, and CPI

| | | | | | Protein (w/w) | | | | | Other | | | Dose weight (mg) of dry vaccine | |
|---|---|---|---|---|---|---|---|---|---|---|---|---|---|---|
| Formulation | Sugar (w/w) | | | | | NZ- | Amino Acid (M) | | MgSO4 | Stabil. | Buffer | | 100 uL | 250 uL |
| Name | Sucrose | Trehalose | Sorbitol | Mannitol | Gelatin | Amine | L-Arg | L-Glu | (w/w) | (w/w) | (w/w) | pH | beads | beads |
| SP01 | 64.2% | | | | 13.5% | 16.9% | | | | | 2.5% | 7.2 | 5.6 | 14.0 |
| SP06 | | | 47.8% | | 23.9% | 23.9% | | | | | 1.4% | 7.2 | 10.0 | 25.0 |
| SP02B | 65.4% | | | | 3.1% | 3.8% | 24.2% | | | | 0.6% | 7.2 | 25.2 | 63.1 |
| SP10 | 51.6% | 20.5% | | | 2.4% | 3.0% | 19.1% | | | | 0.5% | 7.2 | 32.0 | 80.1 |
| SP11 | 39.4% | 26.0% | | | 3.1% | 3.8% | 24.2% | | | | 0.6% | 7.2 | 25.2 | 63.1 |
| SP12 | 26.0% | 39.4% | | | 3.1% | 3.8% | 24.2% | | | | 0.6% | 7.2 | 25.2 | 63.1 |
| SP13 | 20.5% | 51.6% | | | 2.4% | 3.0% | 19.1% | | | | 0.5% | 7.2 | 32.0 | 80.1 |
| SP14 | | 65.4% | | | 3.1% | 3.8% | 24.2% | | | | 0.6% | 7.2 | 25.2 | 63.1 |
| SP15 | 53.9% | | | | 4.2% | 5.2% | 33.0% | | | | 0.8% | 7.2 | 18.4 | 46.1 |
| SP16 | 26.9% | 26.9% | | | 4.2% | 5.2% | 33.0% | | | | 0.8% | 7.2 | 18.4 | 46.1 |
| SP17 | | 53.9% | | | 4.2% | 5.2% | 33.0% | | | | 0.8% | 7.2 | 18.4 | 46.1 |
| SP26 | 71.4% | | | | 3.3% | 4.2% | 17.6% | | | | 0.6% | 7.2 | 23.1 | 57.8 |
| SP27 | 78.5% | | | | 3.7% | 4.6% | 9.7% | | | | 0.7% | 7.2 | 21.0 | 52.5 |
| SP33 | 48.8% | 19.4% | | | 2.3% | 2.9% | 23.3% | | | | 0.4% | 7.2 | 33.9 | 84.7 |
| SP34 | 50.6% | 20.1% | | | 2.4% | 3.0% | 20.6% | | | | 0.4% | 7.2 | 32.7 | 81.7 |
| SP35 | 52.6% | 20.9% | | | 2.5% | 3.1% | 9.7% | 7.8% | | | 0.5% | 7.2 | 31.4 | 78.5 |
| SP36 | 47.0% | 18.7% | | | 2.2% | 2.7% | 14.5% | 11.6% | | | 0.4% | 7.2 | 35.2 | 88.0 |
| SP39 | 50.5% | 20.1% | | | 2.4% | 3.0% | 18.7% | | | 2.1% | 0.4% | 7.2 | 32.7 | 81.8 |
| SP40 | 50.4% | 20.0% | | | 2.4% | 2.9% | 18.6% | | | 2.3% | 0.4% | 7.2 | 32.8 | 82.0 |
| SP43 | 51.6% | 20.5% | | | 2.4% | 3.0% | 19.1% | | | | 0.5% | 6.5 | 32.0 | 80.1 |
| SP44 | 48.5% | 19.3% | | 5.7% | 2.3% | 2.8% | 17.9% | | 0.1% | | 0.5% | 6.5 | 34.0 | 85.1 |
| FDIV-03 | 65.4% | | | | 3.1% | 3.8% | 24.2% | | | | 0.6% | 7.2 | 25.2 | 63.1 |
| FDIV-11 | 42.8% | | 3.1% | 16.6% | 3.3% | 4.2% | 26.3% | | 0.1% | | 0.6% | 7.2 | 23.2 | 58.0 |

The antigen input is around 1% (w/w) and the RMC is around 2% (w/w) in the freeze dried vaccine.

Dose weight of dry vaccine is the weight of one dose amount of vaccine when dried from either 100 uL or 250 uL vaccine blend using the corresponding formulations of Table 1b below.

L-arginine (L-Arg) in SP33 is arginine phosphate, and L-arginine in SP34 is arginine acetic.

In both SP35 and SP36, L-arginine is arginine chloride and L-Glu is sodium glutamic acid.

SP39 contains ectoine and SP40 contains hydroxyectoine as other stabilizers (Other Stabil.).

SP43 and SP44 contains histidine as the buffer in the vaccine blend, all other formulations contain potassium phosphate (KPO4) as buffer.

TABLE 1b

Blending Formulation for Freeze Dried CDV, CPI, CAV2, and CPV

| Formulation | Sugar (w/v) | | | | Protein (w/v) | | Amino Acid (M) | | MgSO4 | Other Stabilizers | Buffer | |
|---|---|---|---|---|---|---|---|---|---|---|---|---|
| Name | Sucrose | Trehalose | Sorbitol | Mannitol | Gelatin | NZ-Amine | L-Arg | L-Glu | (mM) | (w/v) | (10 mM) | pH |
| SP01 | 3.8% | | | | 0.8% | 1.0% | | | | | KPO4 | 7.2 |
| SP06 | | | 5% | | 2.5% | 2.5% | | | | | KPO4 | 7.2 |
| SP02B | 17.1% | | | | 0.8% | 1.0% | 0.3M | | | | KPO4 | 7.2 |
| SP10 | 17.1% | 6.8% | | | 0.8% | 1.0% | 0.3M | | | | KPO4 | 7.2 |
| SP11 | 10.3% | 6.8% | | | 0.8% | 1.0% | 0.3M | | | | KPO4 | 7.2 |
| SP12 | 6.8% | 10.3% | | | 0.8% | 1.0% | 0.3M | | | | KPO4 | 7.2 |
| SP13 | 6.8% | 17.1% | | | 0.8% | 1.0% | 0.3M | | | | KPO4 | 7.2 |
| SP14 | | 17.1% | | | 0.8% | 1.0% | 0.3M | | | | KPO4 | 7.2 |
| SP15 | 10.3% | | | | 0.8% | 1.0% | 0.3M | | | | KPO4 | 7.2 |
| SP16 | 5.2% | 5.2% | | | 0.8% | 1.0% | 0.3M | | | | KPO4 | 7.2 |
| SP17 | | 10.3% | | | 0.8% | 1.0% | 0.3M | | | | KPO4 | 7.2 |
| SP26 | 17.1% | | | | 0.8% | 1.0% | 0.2M | | | | KPO4 | 7.2 |
| SP27 | 17.1% | | | | 0.8% | 1.0% | 0.1M | | | | KPO4 | 7.2 |
| SP33 | 17.1% | 6.8% | | | 0.8% | 1.0% | 0.3M Arg3PO4 | | | | KPO4 | 7.2 |
| SP34 | 17.1% | 6.8% | | | 0.8% | 1.0% | 0.3M ArgAc | | | | KPO4 | 7.2 |
| SP35 | 17.1% | 6.8% | | | 0.8% | 1.0% | 0.15M | 0.15M | | | KPO4 | 7.2 |
| SP36 | 17.1% | 6.8% | | | 0.8% | 1.0% | 0.25M | 0.25M | | | KPO4 | 7.2 |
| SP39 | 17.1% | 6.8% | | | 0.8% | 1.0% | 0.3M | | | 0.71% Ectonine | KPO4 | 7.2 |
| SP40 | 17.1% | 6.8% | | | 0.8% | 1.0% | 0.3M | | | 0.79% Hydroxy-ectonine | KPO4 | 7.2 |
| SP43 | 17.1% | 6.8% | | | 0.8% | 1.0% | 0.3M | | | | Histidine | 6.5 |
| SP44 | 17.1% | 6.8% | | 2% | 0.8% | 1.0% | 0.3M | | 2 mM | | Histidine | 6.5 |
| FDIV-03 | 17.1% | | | | 0.8% | 1.0% | 0.3M | | | | KPO4 | 7.2 |
| FDIV-11 | 10.3% | | 0.75% | 4% | 0.8% | 1.0% | 0.3M | | 2 mM | | KPO4 | 7.2 |

The units for the final amount of each stabilizer in the vaccine is listed at the top of each category. w/v is weight per volume.
KPO4 is potassium phosphate buffer. The pH is the final pH of the vaccine blend when the antigens/viruses are included.
For L-Arg, formulation SP33 and SP34 contains phosphate and the acetic acid salt of L-arginine, respectively. All other L-Arg listed in the table is the chloride salt.

TABLE 2a

Stabilizers and Excipients (w/w) in the Freeze Dried Vaccine Products Containing CPV

| Formulation | Sugar (w/w) | | | Bulking (w/w) | | Protein (w/w) | | L-Arg | KPO4 | Dose weight (mg) of dry vaccine | |
|---|---|---|---|---|---|---|---|---|---|---|---|
| Name | Sucrose | Trehalose | Sorbitol | Gly | Dextran | Gelatin | NZ-Amine | (w/w) | (w/w) | 100 uL beads | 250 uL beads |
| SPCPV-02 | | | 28.1% | 11.2% | 11.2% | 4.5% | 5.6% | 35.5% | 0.8% | 17.1 | 42.8 |
| SPCPV-06 | 28.1% | | | 11.2% | 11.2% | 4.5% | 5.6% | 35.5% | 0.8% | 17.1 | 42.8 |
| SPCPV-10 | | 65.0% | | 16.2% | | 6.5% | 8.1% | | 1.2% | 11.8 | 29.5 |
| SPCPV-13 | | | 38.3% | 9.6% | 9.6% | 3.8% | 4.8% | 30.3% | 0.7% | 20.1 | 50.3 |
| SPCPV-14 | | | 48.0% | 8.0% | 8.0% | 3.2% | 4.0% | 25.3% | 0.6% | 24.1 | 60.3 |
| SPCPV-15 | | | 23.7% | 9.5% | 9.5% | 11.9% | 11.9% | 30.0% | 0.7% | 20.3 | 50.8 |
| SPCPV-17 | | | 34.3% | 13.7% | 13.7% | 17.2% | 17.2% | | 1.0% | 14.0 | 35.0 |
| SPCPV-23 | | | 30.1% | 12.0% | 24.0% | 15.0% | 15.0% | | 0.9% | 16.0 | 40.0 |
| SPCPV-24 | | | 26.7% | 10.7% | 32.1% | 13.4% | 13.4% | | 0.8% | 18.0 | 45.0 |
| SPCPV-26 | | | 40.6% | 10.1% | 20.3% | 12.7% | 12.7% | | 0.8% | 19.0 | 47.5 |

The antigen input is around 1% (w/w) and the RMC is around 2% (w/w) in the freeze dried formulation of the vaccine.
Dose weight of the dry vaccine is the weight of one dose amount of vaccine when dried from either 100 uL or 250 uL vaccine blend using the corresponding formulations of Table 2b below.
L-Arg is arginine chloride; Gly is glycine.

TABLE 2b

Blending Formulation For Freeze Dried CPV

| Formulation | Sugar (w/v) | | | Bulking (w/v) | | Protein (w/v) | | L-Arg | KPO4 | |
|---|---|---|---|---|---|---|---|---|---|---|
| Name | Sucrose | Trehalose | Sorbitol | Glycine | Dextran | Gelatin | NZ-Amine | (M) | (mM) | pH |
| SPCPV-02 | | | 5.0% | 2.0% | 2.0% | 0.8% | 1.0% | 0.3M | 10 mM | 7.2 |
| SPCPV-06 | 5.0% | | | 2.0% | 2.0% | 0.8% | 1.0% | 0.3M | 10 mM | 7.2 |

TABLE 2b-continued

| Blending Formulation For Freeze Dried CPV | | | | | | | | | | |
|---|---|---|---|---|---|---|---|---|---|---|
| | | | | | | | Protein (w/v) | | | |
| Formulation | Sugar (w/v) | | | Bulking (w/v) | | | NZ- | L-Arg | KPO4 | |
| Name | Sucrose | Trehalose | Sorbitol | Glycine | Dextran | Gelatin | Amine | (M) | (mM) | pH |
| SPCPV-10 | | 8.0% | | 2.0% | | 0.8% | 1.0% | | 10 mM | 7.2 |
| SPCPV-13 | | | 8.0% | 2.0% | 2.0% | 0.8% | 1.0% | 0.3M | 10 mM | 7.2 |
| SPCPV-14 | | | 12.0% | 2.0% | 2.0% | 0.8% | 1.0% | 0.3M | 10 mM | 7.2 |
| SPCPV-15 | | | 5.0% | 2.0% | 2.0% | 2.5% | 2.5% | 0.3M | 10 mM | 7.2 |
| SPCPV-17 | | | 5.0% | 2.0% | 2.0% | 2.5% | 2.5% | | 10 mM | 7.2 |
| SPCPV-23 | | | 5.0% | 2.0% | 4.0% | 2.5% | 2.5% | | 10 mM | 7.2 |
| SPCPV-24 | | | 5.0% | 2.0% | 6.0% | 2.5% | 2.5% | | 10 mM | 7.2 |
| SPCPV-26 | | | 8.0% | 2.0% | 4.0% | 2.5% | 2.5% | | 10 mM | 7.2 |

The units for the final amount of each stabilizer in the vaccine is listed at the top of each category. w/v is weight per volume.
KPO4 is potassium phosphate buffer.
The pH is the final pH of the vaccine blend when the antigens/viruses are included.

TABLE 3

| Correlation of Accelerated (45° C. and 37° C.) and Real Time (at 27° C.) Stability Testing for Formulation Screening | | | | | | | | | | | | | | |
|---|---|---|---|---|---|---|---|---|---|---|---|---|---|---|
| | | Virus titer during stability study at different temperature and formulation ranking | | | | | | | | | | | | |
| | | | 45° C. | | | | 37° C. | | | | 27° C. | | | |
| Virus | Formulation | D 0 | wk 1 | wk 2 | wk 4 | Ranking | wk 4 | wk 6 | wk 12 | Ranking | m 6 | m 12 | m 18 | Ranking |
| CDV | SP06 | 7.50 | 4.58 | 4.25 | 2.58 | + | 3.50 | 1.58 | 1.50 | + | 5.33 | 3.88 | 3.67 | + |
| CDV | SP02B | 7.00 | n/a | 5.25 | 5.00 | ++ | 4.67 | 4.83 | 4.00 | ++ | 5.33 | 4.50 | 4.75 | ++ |
| CDV | SP10 | 6.83 | n/a | 5.58 | 5.08 | +++ | 5.33 | 5.17 | 5.25 | +++ | 5.42 | 5.50 | 5.33 | +++ |
| CPI | SP01 | 6.83 | 5.17 | 4.50 | 4.58 | ++ | 4.33 | 3.58 | 2.50 | ++ | 5.08 | 4.67 | 3.92 | ++ |
| CPI | SP06 | 6.67 | 4.58 | 4.17 | 2.50 | + | 3.33 | 2.58 | 1.50 | + | 5.33 | 4.33 | 3.67 | + |
| CPI | SP02B | 6.83 | 5.33 | 4.67 | 4.83 | +++ | 4.58 | 4.25 | 3.75 | +++ | 5.08 | 4.92 | 4.92 | +++ |
| CAV2 | SP01 | 4.00 | 1.58 | 2.33 | n/a | + | 1.50 | 1.50 | n/a | + | 1.58 | 1.50 | 1.67 | + |
| CAV2 | SP15 | 4.58 | 3.17 | 3.33 | n/a | ++ | 2.83 | 3.00 | n/a | ++ | 3.17 | 2.92 | n/a | ++ |
| CAV2 | SP02B | 4.33 | 4.33 | 4.25 | 2.83 | +++ | 3.33 | 3.25 | 1.50 | +++ | 3.67 | 3.58 | 3.67 | +++ |
| CAV2 | SP10 | 4.08 | 4.33 | 4.17 | 3.67 | ++++ | 3.50 | 3.50 | 3.08 | ++++ | 3.92 | 3.75 | 3.83 | ++++ |
| | | D 0 | wk 2 | wk 4 | wk 8 | | m 2 | m 4 | m 6 | | m 6 | m 10 | m 12 | |
| CPV | SPCPV-02 | 4.83 | 4.83 | 4.33 | 4.67 | +++ | 4.50 | 3.83 | 3.67 | +++ | 4.75 | 4.92 | 4.58 | +++ |
| CPV | SPCPV-06 | 4.92 | 3.83 | 3.42 | 3.25 | ++ | 3.83 | 3.17 | 3.33 | ++ | 5.25 | 4.33 | 3.92 | ++ |
| CPV | SPCPV-10 | 5.13 | 3.75 | 3.25 | 2.50 | + | 4.00 | 3.08 | 2.83 | + | 4.50 | 3.83 | 3.50 | + |

n/a indicates that the data is missing due to assay errors or the samples were not tested.
"+" is used to rank the formulations with a greater number of "+" indicating better stability.
The time point is expressed as the combination of day (D), week (wk), or month (m) and duration. For example, D 0 is day 0, wk 1 is week 1, and m 6 is month 6.

TABLE 4

| Freeze Drying Cycles for Vaccines for Frozen Beads Vaccines | | | | |
|---|---|---|---|---|
| Step | Temperature | Time | Ramp Rate | Chamber pressure |
| Loading | −20° C. | 1 Hour | N/A | N/A |
| Freezing | −20° C. to −45° C. | N/A | 1° C./minute | N/A |
| Holding | −45° C. | 1 hour | 1° C./minute | N/A |
| Annealing | −20° C. | N/A | N/A | N/A |
| Holding | −20° C. | 1 hour | N/A | N/A |
| Freezing | −20° C. to −45° C. | N/A | 1° C./minute | N/A |
| Holding | −45° C. | 1 hour | N/A | N/A |
| Primary | −45° C. | 10 minutes | N/A | 30 mTorr |
| Drying | −45° C. to 35° C. | N/A | 0.5° C./minute | 30 mTorr |
| | 35° C. | 9 hours | N/A | 30 mTorr |

TABLE 4-continued

| Freeze Drying Cycles for Vaccines for Frozen Beads Vaccines | | | | |
|---|---|---|---|---|
| Step | Temperature | Time | Ramp Rate | Chamber pressure |
| Secondary Drying | 35° C. | 3 hours | N/A | 255 mTorr |

N/A: not apply

TABLE 5

| Freeze Drying Cycle for Vaccine in Vial | | | | |
|---|---|---|---|---|
| Step | Temperature | Time | Ramp Rate | Chamber pressure |
| Loading | 4° C. | 1 Hour | N/A | N/A |
| Freezing | 4° C. to −50° C. | N/A | 1° C./minute | N/A |

TABLE 5-continued

Freeze Drying Cycle for Vaccine in Vial

| Step | Temperature | Time | Ramp Rate | Chamber pressure |
|---|---|---|---|---|
| Holding | −50° C. | 2 hour | 1° C./minute | N/A |
| Annealing | −15° C. | N/A | N/A | N/A |
| Holding | −15° C. | 2 hours | N/A | N/A |
| Freezing | −15° C. to −30° C. | N/A | 1° C./minute | N/A |
| Holding | −30° C. | 4 hours | N/A | N/A |
| Primary | −30° C. | 40 hours | N/A | 50 mTorr |
| Drying | −30° C. to 10° C. | N/A | 1° C./minute | 200 mTorr |
| | 10° C. | 8 hours | N/A | 200 mTorr |
| Secondary Drying | 10° C. to 35° C. | N/A | 1° C./minute | 200 mTorr |
| | 35° C. | 4 | N/A | 200 mTorr |

N/A: not apply

TABLE 6

Estimated Shelf Life of CDV, CPI, CAV2 and CPV at 27° C. in Different Formulations

| | | Virus Titer at different time at 27° C. | | | | Estimated Shelf |
|---|---|---|---|---|---|---|
| Virus | Formulations | D 0 | m 6 | m 12 | M18 | life at 27° C. |
| CDV | SP02B | 7.00 | 5.33 | 4.50 | 4.75 | ~24 mon |
| CDV | SP10 | 6.83 | 5.42 | 5.50 | 5.33 | >24 mon |
| CPI | SP02B | 6.67 | 5.00 | 4.75 | 4.83 | >18 mon |
| CPI | SP10 | 7.17 | 4.92 | 4.92 | 4.92 | >18 mon |

TABLE 6-continued

Estimated Shelf Life of CDV, CPI, CAV2 and CPV at 27° C. in Different Formulations

| | | Virus Titer at different time at 27° C. | | | | Estimated Shelf |
|---|---|---|---|---|---|---|
| Virus | Formulations | D 0 | m 6 | m 12 | M18 | life at 27° C. |
| CAV | SP02B | 4.33 | 3.67 | 3.58 | 3.67 | ~18 mon |
| CAV | SP10 | 4.08 | 3.92 | 3.75 | 3.83 | >24 mon |
| | | D 0 | m 6 | m 10 | m 12 | |
| CPV | SPCPV-02 | 4.83 | 4.75 | 4.92 | 4.58 | ~18 mon |
| CPV | SPCPV-03 | 5.08 | 4.33 | 4.92 | 4.75 | ~18 mon |

TABLE 7

Several Leading Formulations Identified Using 45° C. Accelerated Stability Testing

| | | Virus Titer at 45° C. | | | | Stability |
|---|---|---|---|---|---|---|
| Virus | Formulation | D 0 | wk 1 | wk 2 | wk 4 | Ranking |
| CDV | SP10 | 7.00 | 5.83 | 5.45 | 5.44 | +++ |
| CDV | SP43 | 7.11 | 6.11 | 6.00 | 5.89 | ++++ |
| CDV | SP44 | 7.44 | 6.50 | 6.28 | 6.11 | +++++ |
| CPI | SP10 | 6.83 | 5.66 | 5.17 | 4.83 | +++ |
| CPI | SP43 | 6.94 | 5.72 | 5.28 | 5.39 | ++++ |
| CPI | SP44 | 7.17 | 6.28 | 5.83 | 5.56 | +++++ |
| CAV2 | SP10 | 4.56 | 4.56 | 4.72 | 4.50 | +++ |
| CAV2 | SP43 | 4.61 | 4.56 | 4.61 | 4.67 | +++ |
| CAV2 | SP44 | 4.67 | 5.22 | 5.00 | 4.61 | ++++ |

TABLE 8

Effects of Buffer and pH on the Virus Stability

| | | | | Virus titer at different time point | | | | | Virus |
|---|---|---|---|---|---|---|---|---|---|
| Virus | Formulation | Buffer | pH | D 0 | 45° C. W 2 | 45° C. W 4 | 27° C. m 3 | 27° C. m 6 | Stability Ranking |
| CDV | IB3-01 | KPO4 | 6.5 | n/a | 5.58 | 4.67 | 6.00 | 5.50 | +++++ |
| CDV | IB3-02 | KPO4 | 7.2 | 6.63 | 4.58 | 3.00 | 5.38 | 5.25 | +++ |
| CDV | IB3-03 | KPO4 | 7.6 | 6.88 | 4.00 | 2.00 | 5.00 | 4.63 | + |
| CDV | IB3-04 | Histidine | 6.5 | 7.13 | 5.33 | 4.33 | 5.50 | 5.38 | ++++ |
| CDV | IB3-05 | Histidine | 7.2 | 7.00 | 4.50 | 3.17 | 5.25 | 5.25 | +++ |
| CDV | IB3-06 | Histidine | 7.6 | 6.88 | 4.08 | 2.83 | 4.75 | 5.13 | ++ |
| CDV | IB3-07 | BTP | 6.5 | 6.88 | 5.25 | 3.83 | 5.75 | 5.38 | ++++ |
| CDV | IB3-08 | MOPS | 6.5 | 7.00 | 4.75 | 3.92 | 5.63 | 5.38 | ++++ |
| CPI | IB3-01 | KPO4 | 6.5 | n/a | 5.42 | 4.58 | 6.25 | 5.25 | +++++ |
| CPI | IB3-02 | KPO4 | 7.2 | 6.50 | 4.50 | 3.42 | 5.38 | 4.75 | +++ |
| CPI | IB3-03 | KPO4 | 7.6 | 6.38 | 3.75 | 2.17 | 4.75 | 4.25 | + |
| CPI | IB3-04 | Histidine | 6.5 | 7.00 | 5.33 | 4.17 | 5.75 | 4.88 | ++++ |
| CPI | IB3-05 | Histidine | 7.2 | 6.88 | 4.25 | 3.00 | 5.25 | 4.63 | +++ |
| CPI | IB3-06 | Histidine | 7.6 | 6.88 | 4.17 | 3.00 | 5.13 | 4.88 | ++ |
| CPI | IB3-07 | BTP | 6.5 | 6.75 | 4.75 | 4.08 | 5.13 | 5.25 | ++++ |
| CPI | IB3-08 | MOPS | 6.5 | 7.00 | 5.00 | 4.00 | 5.75 | 5.13 | ++++ |
| CAV2 | IB3-01 | KPO4 | 6.5 | 4.80 | 4.50 | 4.50 | 5.25 | 5.38 | ++++ |
| CAV2 | IB3-02 | KPO4 | 7.2 | 5.18 | 4.58 | 4.42 | 5.00 | 5.00 | +++ |
| CAV2 | IB3-03 | KPO4 | 7.6 | 4.18 | 4.25 | 4.67 | 5.38 | 5.13 | +++ |
| CAV2 | IB3-04 | Histidine | 6.5 | 4.68 | 4.58 | 5.08 | 5.50 | 5.25 | ++++ |
| CAV2 | IB3-05 | Histidine | 7.2 | 4.80 | 4.58 | 4.50 | 5.25 | 5.13 | +++ |
| CAV2 | IB3-06 | Histidine | 7.6 | 4.93 | 4.42 | 4.75 | 4.75 | 5.00 | ++ |
| CAV2 | IB3-07 | BTP | 6.5 | 4.55 | 4.83 | 4.75 | 5.13 | 5.75 | +++++ |
| CAV2 | IB3-08 | MOPS | 6.5 | 4.55 | 4.75 | 4.67 | 4.75 | 5.63 | ++++ |
| CPV | IB3-01 | KPO4 | 6.5 | 4.25 | 2.92 | 3.25 | 4.63 | n/a | ++ |
| CPV | IB3-02 | KPO4 | 7.2 | 4.25 | 3.67 | 4.33 | 5.63 | n/a | +++ |
| CPV | IB3-03 | KPO4 | 7.6 | 4.00 | 3.83 | 4.75 | 5.50 | n/a | +++ |
| CPV | IB3-04 | Histidine | 6.5 | n/a | 4.17 | 4.00 | 5.25 | n/a | +++ |
| CPV | IB3-05 | Histidine | 7.2 | 4.25 | 4.25 | 4.83 | 5.50 | n/a | ++++ |
| CPV | IB3-06 | Histidine | 7.6 | 3.50 | 3.67 | 4.92 | 5.50 | n/a | ++++ |

TABLE 8-continued

Effects of Buffer and pH on the Virus Stability

| Virus | Formulation | Buffer | pH | D 0 | Virus titer at different time point 45° C. W 2 | 45° C. W 4 | 27° C. m 3 | 27° C. m 6 | Virus Stability Ranking |
|---|---|---|---|---|---|---|---|---|---|
| CPV | IB3-07 | BTP | 6.5 | 4.88 | 3.58 | 3.83 | 4.88 | n/a | ++ |
| CPV | IB3-08 | MOPS | 6.5 | 4.50 | 3.92 | 4.00 | 5.38 | n/a | +++ |

TABLE 9a

Non-Reducing Oligosaccharide Content and Total Non-Reducing Oligosaccharide of Blend Formulations Used in Table 9b

| Formulations | Sugar concentration (w/v) Sucrose | Trehalose | Total sugar content (w/v) |
|---|---|---|---|
| SP02B | 17.1% | — | 17.1% |
| SP10 | 17.1% | 6.8% | 23.9% |
| SP11 | 10.3% | 6.8% | 17.1% |
| SP12 | 6.8% | 10.3% | 17.1% |
| SP13 | 6.8% | 17.1% | 23.9% |

TABLE 9a-continued

Non-Reducing Oligosaccharide Content and Total Non-Reducing Oligosaccharide of Blend Formulations Used in Table 9b

| Formulations | Sugar concentration (w/v) Sucrose | Trehalose | Total sugar content (w/v) |
|---|---|---|---|
| SP14 | — | 17.1% | 17.1% |
| SP15 | 10.3% | — | 10.3% |
| SP16 | 5.2% | 5.2% | 10.3% |
| SP17 | — | 10.3% | 10.3% |

TABLE 9b

Effects of Sugar Concentration on the Stability of Freeze Dried CDV, CPI, and CAV2

| Virus | Formulation | D 0 | Virus Titer at different time point at 45° C. and 37° C. 45° C. wk 2 | 45° C. wk 4 | 45° C. wk 8 | 37° C. wk 2 | 37° C. wk 4 | 37° C. wk 6 | 37° C. wk 12 | Stability Ranking |
|---|---|---|---|---|---|---|---|---|---|---|
| CDV | SP02B | 7.00 | 5.25 | 5.00 | 4.67 | 4.92 | 4.67 | 4.83 | 4.00 | ++ |
| CDV | SP10 | 6.83 | 5.58 | 5.08 | 5.50 | 5.25 | 5.33 | 5.17 | 5.25 | ++++ |
| CDV | SP11 | 6.92 | 5.00 | 5.00 | n/a | 5.58 | 5.17 | 4.83 | n/a | +++ |
| CDV | SP12 | 6.75 | 5.00 | 5.00 | n/a | 5.17 | 4.42 | 4.67 | n/a | ++ |
| CDV | SP13 | 7.17 | 5.08 | 5.00 | 4.75 | 5.08 | 5.33 | 5.08 | 5.13 | ++++ |
| CDV | SP14 | 6.92 | 4.83 | 4.92 | 5.17 | 5.33 | 4.92 | 4.83 | 4.38 | ++ |
| CDV | SP15 | 7.00 | 5.17 | 4.92 | n/a | 4.92 | 4.88 | 4.67 | n/a | ++ |
| CDV | SP16 | 6.75 | 5.00 | 4.33 | n/a | 4.92 | 4.75 | 4.50 | n/a | + |
| CDV | SP17 | 6.83 | 4.33 | 4.75 | n/a | 4.92 | 4.33 | 4.08 | n/a | + |
| CPI | SP02B | 6.67 | 4.67 | 4.58 | 4.42 | 4.75 | 4.67 | 4.00 | 2.92 | ++ |
| CPI | SP10 | 7.17 | 5.17 | 4.92 | 4.67 | 5.17 | 5.00 | 4.33 | 3.75 | ++++ |
| CPI | SP11 | 6.67 | 5.17 | 4.78 | n/a | 5.00 | 4.75 | 4.42 | n/a | +++ |
| CPI | SP12 | 6.92 | 4.92 | 4.75 | n/a | 4.92 | 4.67 | 3.75 | n/a | ++ |
| CPI | SP13 | 6.92 | 5.33 | 4.83 | 4.67 | 4.67 | 4.67 | 4.50 | 4.25 | ++++ |
| CPI | SP14 | 6.67 | 4.92 | 4.83 | 4.33 | 4.75 | 4.58 | 4.33 | 2.50 | ++ |
| CPI | SP15 | 7.08 | 5.08 | 4.92 | n/a | 4.92 | 4.67 | 4.00 | n/a | ++ |
| CPI | SP16 | 6.83 | 4.92 | 4.58 | n/a | 5.00 | 4.67 | 4.00 | n/a | ++ |
| CPI | SP17 | 6.67 | 4.58 | 4.17 | n/a | 4.92 | 4.33 | 3.58 | n/a | + |
| CAV2 | SP02B | 4.33 | 4.33 | 4.25 | 2.83 | 3.33 | 3.33 | 3.25 | 1.50 | ++ |
| CAV2 | SP10 | 4.08 | 4.33 | 4.17 | 3.67 | 3.58 | 3.50 | 3.50 | 3.08 | +++ |
| CAV2 | SP11 | 4.25 | 3.58 | 3.75 | n/a | 3.00 | 3.17 | 2.75 | n/a | + |
| CAV2 | SP12 | 4.58 | 3.92 | 3.83 | n/a | 3.33 | 3.67 | 3.17 | n/a | ++ |
| CAV2 | SP13 | 4.42 | 4.50 | 4.42 | 3.33 | 3.58 | 3.75 | 4.17 | 3.08 | +++ |
| CAV2 | SP14 | 4.33 | 3.92 | 3.92 | 3.50 | 3.58 | 3.58 | 3.42 | 3.25 | +++ |
| CAV2 | SP15 | 4.58 | 3.17 | 3.33 | n/a | 2.83 | 2.83 | 3.00 | n/a | ++ |
| CAV2 | SP16 | 4.08 | 3.33 | 3.17 | n/a | 2.92 | 2.58 | 2.50 | n/a | + |
| CAV2 | SP17 | 4.33 | 2.58 | 2.58 | n/a | 2.33 | 2.67 | 2.92 | n/a | + |

n/a: data point not available

TABLE 10

Effects of L-Arginine Concentration in Blend on the Virus Stability

| | Formulation | | Virus titer during stability testing at 45° C. and 37° C. | | | | | | | | |
|---|---|---|---|---|---|---|---|---|---|---|---|
| Virus | Name | L-Arg | D 0 | 45° C. wk 1 | 45° C. wk 2 | 45° C. wk 4 | 45° C. wk 8 | 37° C. m 2 | 37° C. m 4 | 37° C. m 6 | Stability Ranking |
| CDV | SP02B | 0.3M | 5.75 | 5.50 | 5.83 | 5.58 | 4.83 | 5.25 | 5.42 | 4.83 | +++ |
| CDV | SP26 | 0.2M | 6.58 | 5.58 | 5.83 | 5.33 | 4.33 | 5.17 | 4.75 | 4.83 | ++ |
| CDV | SP27 | 0.1M | n/a | 6.33 | 5.25 | 4.92 | 4.33 | 5.42 | 4.25 | 4.58 | + |
| CPI | SP02B | 0.3M | 7.00 | 5.08 | 5.25 | 4.83 | 4.92 | 4.75 | 5.17 | 4.42 | +++ |
| CPI | SP26 | 0.2M | 6.83 | 5.42 | 5.67 | 4.67 | 4.17 | 5.00 | 4.50 | 4.42 | ++ |
| CPI | SP27 | 0.1M | 6.67 | 5.33 | 4.83 | 4.58 | 4.25 | 4.58 | 4.42 | 4.00 | + |
| CAV2 | SP02B | 0.3M | 4.00 | 3.75 | 3.42 | 3.58 | 3.67 | 3.67 | 3.83 | 3.00 | +++ |
| CAV2 | SP26 | 0.2M | 4.33 | 3.42 | 3.25 | 2.92 | 3.67 | 3.25 | 3.50 | 1.67 | + |
| CAV2 | SP27 | 0.1M | 4.33 | 3.33 | 2.83 | 2.50 | 2.67 | 3.33 | 2.92 | 2.42 | + |

n/a: data point not available

TABLE 11a

Onset Tg of Freeze Dried Beads with Different Arginine Salts and in Combination with Glutamic Acid

| | Stabilizers | | |
|---|---|---|---|
| Formulation | Arginine | Glutamic Acid | Onset Tg (C.) |
| SP10 | 0.3M ArgCl | | 58.7 |
| SP33 | 0.3M Arg3PO4 | | 80.9 |
| SP34 | 0.3M ArgAc | | 36.1 |

TABLE 11a-continued

Onset Tg of Freeze Dried Beads with Different Arginine Salts and in Combination with Glutamic Acid

| | Stabilizers | | |
|---|---|---|---|
| Formulation | Arginine | Glutamic Acid | Onset Tg (C.) |
| SP35 | 0.15M ArgCl | 0.15M Glu | 52.9 |
| SP36 | 0.25M ArgCl | 0.25M Glu | 27.8 |

TABLE 11b

Effects of Different Arginine Salts and Glutamic Acid on CDV, CAV2, and CPI Stability

| | | Virus titer during stability studies at 45° C. or 37° C. | | | | | | | |
|---|---|---|---|---|---|---|---|---|---|
| Virus | Formulation | D 0 | 45° C. wk 1 | 45° C. wk 2 | 45° C. wk 4 | 45° C. wk 8 | 37° C. m 2 | 37° C. m 4 | 27° C. m 7 | Stability Ranking |
| CDV | SP10 | 6.92 | 6.00 | 5.50 | 5.50 | 5.33 | 5.50 | 5.08 | 5.67 | +++ |
| CDV | SP33 | 7.08 | 4.75 | 4.83 | 4.25 | 3.50 | 5.00 | 4.25 | 4.50 | + |
| CDV | SP34 | 7.50 | 5.75 | 5.50 | 5.42 | 4.83 | 5.67 | 5.17 | 5.67 | +++ |
| CDV | SP35 | 7.25 | 5.67 | 5.33 | 5.42 | 5.25 | 5.58 | 5.17 | 5.42 | +++ |
| CDV | SP36 | 7.00 | 6.17 | 5.42 | 4.92 | 3.58 | 5.75 | 4.83 | 6.00 | +++ |
| CPI | SP10 | 6.83 | 5.42 | 5.08 | 5.00 | 4.67 | 5.08 | 5.33 | 5.08 | +++ |
| CPI | SP33 | 6.83 | 4.92 | 4.83 | 3.75 | 3.25 | 4.58 | 3.83 | 4.00 | + |
| CPI | SP34 | 6.67 | 5.50 | 5.42 | 4.42 | 4.75 | 5.50 | 4.83 | 5.58 | +++ |
| CPI | SP35 | 6.58 | 5.67 | 5.33 | 5.08 | 4.25 | 5.25 | 4.50 | 5.25 | ++ |
| CPI | SP36 | 6.58 | 5.83 | 5.83 | 4.58 | 3.83 | 5.25 | 5.08 | 5.33 | +++ |
| CAV2 | SP10 | 4.25 | 4.25 | 4.42 | 4.25 | 4.00 | 4.00 | 4.42 | 4.33 | +++ |
| CAV2 | SP33 | 4.00 | 4.33 | 4.33 | 4.00 | 3.08 | 3.58 | 3.92 | 3.83 | ++ |
| CAV2 | SP34 | 4.50 | 4.42 | 4.58 | 4.17 | 4.33 | 3.92 | 4.58 | 4.33 | +++ |
| CAV2 | SP35 | 4.50 | 4.83 | 4.17 | 4.25 | 4.00 | 4.00 | 4.58 | 4.08 | +++ |
| CAV2 | SP36 | 4.58 | 4.67 | 4.75 | 4.17 | 3.83 | 4.08 | 4.50 | 4.42 | +++ |

TABLE 12

Effect of Mannitol and Glycine as Stabilizers for 4-Way Vaccine

| | | Virus Titer ($Log_{10}$ $TCID_{50}$)after storage at 45° C. | | | | | | | |
|---|---|---|---|---|---|---|---|---|---|
| | Bulking | CDV | | CAV2 | | CPI | | CPV | |
| Formulation | Stabilizer | D 0 | w 2 | D 0 | w 2 | D 0 | w 2 | D 0 | w 2 |
| IB1-02 | Mannitol | 7.75 | 4.50 | 4.83 | 4.67 | 7.25 | 4.17 | 5.83 | 5.17 |
| IB1-06 | Glycine | 7.75 | 3.58 | 5.25 | 4.25 | 8.00 | 3.83 | 6.33 | 5.42 |
| IB1-10 | — | 7.58 | 2.83 | 4.83 | 4.08 | 7.33 | 3.25 | 6.58 | 4.92 |

D 0 is the titer of the virus post lyophilization and w 2 is virus titer after storage at 45° C. for 2 weeks.

The difference between formulations IB1-02, IB1-06, and IB1-10 is the bulking stabilizer. IB1-02 contains 4% Mannitol, IB1-06 contains 2% Glycine whereas, IB1-10 contains no bulking stabilizer.

TABLE 13

Effects of Ectoine and Hydroxyectoine on Virus Stability

| Virus | Formulation | Virus titer during stability testing D 0 | 45° C. wk 1 | 45° C. wk 2 | 45° C. wk 4 | 45° C. wk 8 | 37° C. m 2 | 37° C. m 4 | 27° C. m 7 | Stability Ranking |
|---|---|---|---|---|---|---|---|---|---|---|
| CDV | SP10 | 6.92 | 6.00 | 5.50 | 5.50 | 5.33 | 5.50 | 5.08 | 5.67 | +++ |
| CDV | SP39 | 7.50 | 5.50 | 5.67 | 5.58 | 5.17 | 5.67 | 5.67 | 5.67 | +++ |
| CDV | SP40 | 6.92 | 5.67 | 5.58 | 5.58 | 5.42 | 5.92 | 5.50 | 6.42 | ++++ |
| CPI | SP10 | 6.83 | 5.42 | 5.08 | 5.00 | 4.67 | 5.08 | 5.33 | 5.08 | +++ |
| CPI | SP39 | 6.50 | 5.92 | 5.50 | 4.92 | 4.92 | 5.25 | 5.33 | 5.08 | +++ |
| CPI | SP40 | 6.50 | 5.75 | 5.25 | 5.00 | 5.17 | 5.33 | 5.25 | 5.42 | ++++ |
| CAV2 | SP10 | 4.25 | 4.25 | 4.42 | 4.25 | 4.00 | 4.00 | 4.42 | 4.33 | +++ |
| CAV2 | SP39 | 4.50 | 5.00 | 4.83 | 4.25 | 3.75 | 4.17 | 4.67 | 4.17 | +++ |
| CAV2 | SP40 | 3.92 | 4.25 | 4.67 | 4.08 | 3.92 | 4.50 | 4.50 | 4.00 | +++ |

TABLE 14

Effects of Sorbitol, Protein, and Arginine on CPV Potency and Dry Vaccine Physical Stability

| | Excipients | | | Virus titer at various time point | | | | | | | | | Potency | Physical |
|---|---|---|---|---|---|---|---|---|---|---|---|---|---|---|
| | | | | Pre- | | 45° C. | | | 37° C. | | | 27° C. | Stability | Stability |
| Formulations | Sorbitol | Protein | L-Arg | Lyo | D 0 | w 1 | w 2 | w 4 | m 2 | m 4 | m 6 | m 6 | ranking | ranking |
| SPCPV-02 | 5% | 1xGN | 0.3M | 4.80 | 5.08 | 5.33 | 5.00 | 4.33 | 4.36 | 5.17 | 4.42 | 5.17 | +++ | ++ |
| SPCPV-13 | 8% | 1xGN | 0.3M | 5.30 | 5.17 | 5.25 | 4.83 | 4.25 | 4.75 | 5.58 | 4.75 | 5.58 | ++++ | + |
| SPCPV-14 | 12% | 1xGN | 0.3M | 5.05 | 5.08 | 5.25 | 4.92 | 4.33 | 4.42 | 5.58 | 5.00 | 5.58 | ++++ | + |
| SPCPV-15 | 5% | 2.5xGN | 0.3M | 5.05 | 5.17 | 5.17 | 4.83 | 4.17 | 4.08 | 5.25 | 4.67 | 5.00 | +++ | +++ |
| SPCPV-17 | 5% | 2.5xGN | — | 5.30 | 5.42 | 4.92 | 4.83 | 3.92 | 4.33 | 5.08 | 4.58 | 5.00 | +++ | +++ |

Virus titer at Pre-Lyo is the titer of the virus in the vaccine blend prior to freeze drying (lyophilization).
1xGN is 0.8% (w/v) Gelatin and 1.0% (w/v) NZ Amine. 2.5xGN is 2.5% (w/v) Gelatin and 2.5% (w/v) NZ Amine.

TABLE 15

Effects of Sorbitol and Dextran on CPV stability

| | Excipients (w/v) | | Virus titer after storage at 45° C. | | | | Potency Stability | Physical Stability |
|---|---|---|---|---|---|---|---|---|
| Formulations | Sorbitol | Dextran | D 0 | wk 1 | wk 2 | wk 4 | Ranking | Ranking |
| SP-CPV-17 | 5% | 2% | 4.83 | 4.39 | 3.95 | 3.83 | +++ | +++ |
| SP-CPV-23 | 5% | 4% | 5.17 | 4.33 | 4.05 | 4.00 | +++ | ++++ |
| SP-CPV-24 | 5% | 6% | 4.94 | 4.11 | 3.61 | 3.55 | + | +++++ |
| SP-CPV-26 | 8% | 4% | 5.83 | 4.45 | 4.78 | 4.33 | +++++ | ++++ |

The dextran used has a molecular weight of 70k.
The physical stability ranking is based on the physical structure of the beads after freeze drying, which were determined at different times during the storage at 45° C.

TABLE 16

Effects of Different Drying Formats on Virus Stability

| Freeze dry | | Virus Titer during stability testing at 45° C. CDV | | | CPI | | | CAV2 | | |
|---|---|---|---|---|---|---|---|---|---|---|
| Format | Formulation | D 0 | wk 2 | wk 4 | D 0 | wk 2 | wk 4 | D 0 | wk 2 | wk 4 |
| Beads | SP02B | n/a | 5.25 | 5.00 | 6.67 | 4.67 | 4.58 | 4.33 | 4.33 | 4.25 |
| Vial | FDIV-03 | 7.25 | 5.00 | 4.92 | 7.13 | 5.42 | 4.92 | 4.63 | n/a | 4.25 |

n/a, the titer data for this time point is not available due to assay invalidation.

We claim:

1. A dry formulation of a vaccine that comprises a live attenuated virus, 30% to 80% (w/w) of a non-reducing oligosaccharide, 5% to 40% (w/w) of an amino acid stabilizer, 2% to 20% (w/w) of a protein stabilizer, and a buffer having a pH of 6.0 to 8.0;

wherein the live attenuated virus is selected from the group consisting of a distemper virus, an adenovirus, a parainfluenza virus, and any combination thereof.

2. The dry formulation of claim 1, that further comprises 2% to 25% (w/w) of a bulking stabilizer; wherein the ratio of the bulking stabilizer to the non-reducing oligosaccharide is 0.05 to 0.40.

3. The dry formulation of claim 1, wherein the live attenuated virus is a live attenuated canine virus selected from the group consisting of a canine distemper virus (CDV), a canine adenovirus type 2 (CAV2), a canine parainfluenza virus (CPI), and any combination thereof.

4. The dry formulation of claim 3, further comprising canine parvovirus (CPV) and 2% to 5% (w/w) sorbitol.

5. A method of vaccinating a canine against a canine virus selected from the group consisting of canine distemper virus (CDV), canine adenovirus type 2 (CAV2), canine parainfluenza virus (CPI), canine parvovirus (CPV) and any combination thereof, comprising mixing the dry formulation of claim 4 with a pharmaceutically acceptable carrier to form a liquid vaccine and then administering the liquid vaccine to the canine.

6. The dry formulation of claim 1, further comprising a parvovirus (CPV) and 2% to 5% (w/w) sorbitol.

7. A method of vaccinating an animal against a virus selected from the group consisting of distemper virus, adenovirus, parainfluenza virus, parvovirus, and any combination thereof, comprising mixing the dry formulation of claim 6 with a pharmaceutically acceptable carrier to form a liquid vaccine and then administering the liquid vaccine to the animal.

8. The dry formulation of claim 1, wherein the amino acid stabilizer is arginine.

9. The dry formulation of claim 8, wherein the amino acid stabilizer further comprises glutamate.

10. The dry formulation of claim 1, that prior to being dried the vaccine had been treated by a process selected from the group consisting of applying it to a membrane, freezing it into beads, freezing it in vials, spray drying, and spray freeze drying.

11. The dry formulation of claim 1, wherein the non-reducing oligosaccharide is a combination of 20% to 80% (w/w) sucrose and 18% to 66% (w/w) trehalose; the bulking stabilizer is 5% to 17% (w/w) mannitol; the amino acid stabilizer is 9% to 34% (w/w); wherein the protein stabilizer comprises 2% to 5% (w/w) gelatin and 2% to 6% (w/w) of a proteolytic hydrolysate of whole casein; and wherein the ratio of the bulking stabilizer to the non-reducing oligosaccharide is 0.08 to 0.37.

12. The dry formulation of claim 11, wherein the non-reducing oligosaccharide is a combination of 45% to 60% (w/w) sucrose and 15% to 25% (w/w) trehalose; the bulking stabilizer is 5% to 17% (w/w) mannitol; the amino acid stabilizer is 10% to 25% (w/w) arginine; and wherein the protein stabilizer comprises 1.5% to 3.5% (w/w) gelatin and 2% to 4% (w/w) of a proteolytic hydrolysate of whole casein.

13. A method of making a dry formulation of a room temperature stable vaccine formulation comprising a live attenuated virus:

a. preparing a vaccine formulation by combining a therapeutically effective amount of a live attenuated canine virus with 8% to 30% (w/v) of a non-reducing oligosaccharide, 1% to 6% (w/v) of a bulking stabilizer, 0.1M to 0.5 M of an amino acid stabilizer, 0.9% to 10% (w/v) of a protein stabilizer, and a buffer having a pH of 6.0 to 8.0; wherein the ratio of the bulking stabilizer to the non-reducing oligosaccharide is 0.05 to 0.40; and b. drying the vaccine formulation of step a. under vacuum to make a room temperature stable dry formulation;

wherein the live attenuated virus is selected from the group consisting of a distemper virus, an adenovirus, a parainfluenza virus, and any combination thereof.

14. A dry formulation of a vaccine that comprises a live attenuated parvovirus, 10% to 80% (w/w) of a sugar alcohol, 10% to 70% (w/w) of a bulking stabilizer, 4% to 50% (w/w) of a protein stabilizer, and a buffer having a pH of 6.8 to 8.0.

15. The dry formulation of a vaccine of claim 14, wherein the live attenuated parvovirus is a live attenuated canine parvovirus (CPV).

16. The dry formulation of a vaccine of claim 15, that comprises 23% to 49% (w/w) of a sugar alcohol, 16% to 50% (w/w) of a bulking stabilizer, 7% to 36% (w/w) of a protein stabilizer, and a buffer having a pH of 6.8 to 8.0.

17. The dry formulation of claim 14 wherein the sugar alcohol is sorbitol, the bulking stabilizer is a combination of dextran and glycine, the protein stabilizer is a combination of gelatin and a proteolytic hydrolysate of whole casein.

18. A vaccine comprising a dry formulation that comprises a live attenuated virus, 30% to 80% (w/w) of a non-reducing oligosaccharide, 5% to 40% (w/w) of an amino acid stabilizer, 2% to 20% (w/w) of a protein stabilizer, and a buffer having a pH of 6.0 to 8.0; wherein the live attenuated virus is selected from the group consisting of a distemper virus, an adenovirus, a parainfluenza virus, a recombinant virus vector that encodes and expresses a heterologous antigen, and any combination thereof; combined with the dry formulation of claim 14, and a liquid pharmaceutically acceptable carrier.

19. The vaccine of claim 18, wherein the live attenuated virus is a live attenuated canine virus selected from the group consisting of a canine distemper virus (CDV), a canine adenovirus type 2 (CAV2), a canine parainfluenza virus (CPI), a recombinant canine parainfluenza virus vector (rCPI) that encodes and expresses a heterologous antigen, and any combination thereof; and wherein the live attenuated parvovirus is a live attenuated canine parvovirus (CPV).

20. A method of vaccinating a canine against a canine virus selected from the group consisting of canine distemper virus, canine adenovirus type 2, canine parainfluenza virus, canine parvovirus and any combination thereof, comprising administering the vaccine of claim 19 to the canine.

* * * * *